(12) United States Patent
Takebe et al.

(10) Patent No.: US 9,976,905 B2
(45) Date of Patent: May 22, 2018

(54) SURFACE CHARACTERISTIC MEASUREMENT DEVICE

(71) Applicant: Konica Minolta, Inc., Tokyo (JP)

(72) Inventors: Yosuke Takebe, Osaka (JP); Yoshihisa Abe, Osaka (JP)

(73) Assignee: Konica Minolta, Inc., Tokyo (JP)

( * ) Notice: Subject to any disclaimer, the term of this patent is extended or adjusted under 35 U.S.C. 154(b) by 0 days. days.

(21) Appl. No.: 15/313,514

(22) PCT Filed: Apr. 20, 2015

(86) PCT No.: PCT/JP2015/061983
§ 371 (c)(1),
(2) Date: Nov. 22, 2016

(87) PCT Pub. No.: WO2015/178142
PCT Pub. Date: Nov. 26, 2015

(65) Prior Publication Data
US 2017/0199079 A1    Jul. 13, 2017

(30) Foreign Application Priority Data
May 23, 2014    (JP) ................. 2014-106606

(51) Int. Cl.
*G01N 21/00* (2006.01)
*G01J 3/50* (2006.01)
(Continued)

(52) U.S. Cl.
CPC .............. *G01J 3/50* (2013.01); *G01N 21/27* (2013.01); *G01N 21/57* (2013.01)

(58) Field of Classification Search
CPC ...... G01J 3/02; G01J 3/50; G01J 3/51; G01N 21/57; G01N 21/27; G01N 21/65
See application file for complete search history.

(56) References Cited

U.S. PATENT DOCUMENTS 4,886,355 A * 12/1989 Keane ............... G01J 3/02
                                                      356/328
5,377,000 A * 12/1994 Berends ............ G01J 3/51
                                                      356/407
(Continued)

FOREIGN PATENT DOCUMENTS

EP    2 163 869 A2    3/2010
JP    H08-35937 A     2/1996
(Continued)

OTHER PUBLICATIONS

International Search Report issued in corresponding International Application No. PCT/JP2015/061983 dated Jul. 14, 2015, and English translation thereof (5 pages).
(Continued)

*Primary Examiner* — Abdullahi Nur
(74) *Attorney, Agent, or Firm* — Osha Liang LLP

(57) ABSTRACT

Since both gloss and a reflection characteristic are measured by one surface characteristic measurement device, a gloss measurement target area and a reflection characteristic measurement target area are appropriately set. A gloss measurement instrument and a color measurement instrument are integrated with a gloss colorimeter. The gloss measurement instrument illuminates an illumination target face by illumination light, receives reflected light generated by a regular reflection of the illumination light on the illumination target face, and outputs a measurement result for the reflected light. A size of the gloss measurement target area can be changed. The color measurement instrument illuminates the illumination target face by annular illumination light, receives reflected light generated by a reflection of the annular illumination light on the illumination target face, and outputs a measurement result for the reflected light. A (Continued)

size of the reflection characteristic measurement target area can be changed.

20 Claims, 17 Drawing Sheets

(51) Int. Cl.
  *G01N 21/57* (2006.01)
  *G01N 21/27* (2006.01)

(56) References Cited

U.S. PATENT DOCUMENTS

| | | |
|---|---|---|
| 8,085,409 B2 | 12/2011 | Aso et al. |
| 2005/0073688 A1 | 4/2005 | Sperling |

FOREIGN PATENT DOCUMENTS

| | | |
|---|---|---|
| JP | H10-26587 A | 1/1998 |
| JP | 2005-024562 A | 1/2005 |

OTHER PUBLICATIONS

Written Opinion of the International Searching Authority issued in corresponding International Application No. PCT/JP2015/061983 dated Jul. 14, 2015, and English translation thereof (12 pages).
Extended European Search Report in counterpart European Application No. 15 79 5513.9 dated Nov. 15, 2017 (11 pages).

\* cited by examiner

SURFACE CHARACTERISTIC MEASUREMENT DEVICE

TECHNICAL FIELD

The present invention relates to a surface characteristic measurement device.

BACKGROUND ART

When surface characteristics such as gloss, color, haze, and a film thickness of a sample are measured, it is desirable to change a measurement diameter depending on the sample. For example, when the surface characteristics of the sample are not uniform, it is desirable to relatively increase the measurement diameter. On the other hand, when the sample is small or has a curved surface, it is desirable to relatively decrease the measurement diameter.

Meanwhile, there is proposed a surface characteristic measurement device capable of measuring both gloss and a reflection characteristic other than the gloss. Parent Literature 1 discloses an example thereof.

CITATION LIST

Patent Literature

Patent Literature 1: JP 2005-24562 A

SUMMARY OF INVENTION

In the conventional surface characteristic measurement device capable of measuring both the gloss and the reflection characteristic other than the gloss, a measurement diameter cannot be changed and thus a gloss measurement target area and a reflection characteristic measurement target area cannot be appropriately set. For this reason, a measurer who wants to appropriately set the gloss measurement target area and the reflection characteristic measurement target area needs to prepare a glossmeter and a reflection characteristic measurement device and change at device to be used depending on the sample. Such a change in device is complex.

Embodiments of the present invention provide the ability to measure both gloss and a reflection characteristic by one surface characteristic measurement device and to appropriately set a gloss measurement target area and a reflection characteristic measurement target area.

In the surface characteristic measurement device, the gloss measurement instrument and the reflection characteristic measurement instrument are integrated with each other. The gloss measurement instrument illuminates an illumination target face by first illumination light, receives first reflected light generated by a regular reflection of the first illumination light on the illumination target face, and outputs a measurement result for the first reflected light. The size of the gloss measurement target area can be changed. The reflection characteristic measurement instrument illuminates an illumination target face by second illumination light, receives second reflected light generated by a reflection of the second illumination light on the illumination target face, and outputs a measurement result for the second reflected light. The size of the reflection characteristic measurement target area can be changed.

Advantageous Effects of Invention

Since one surface characteristic measurement device can measure both gloss and a reflection characteristic, a gloss measurement target area and a reflection characteristic measurement target area are appropriately set.

These and other objects, features, aspects, and advantages of the present invention will become more apparent by the following detailed description of the present invention in conjunction with the accompanying drawings.

DESCRIPTION OF EMBODIMENTS

1 First Embodiment

1.1 Gloss Colorimeter

A first embodiment relates to a gloss colorimeter.

Figure 1:
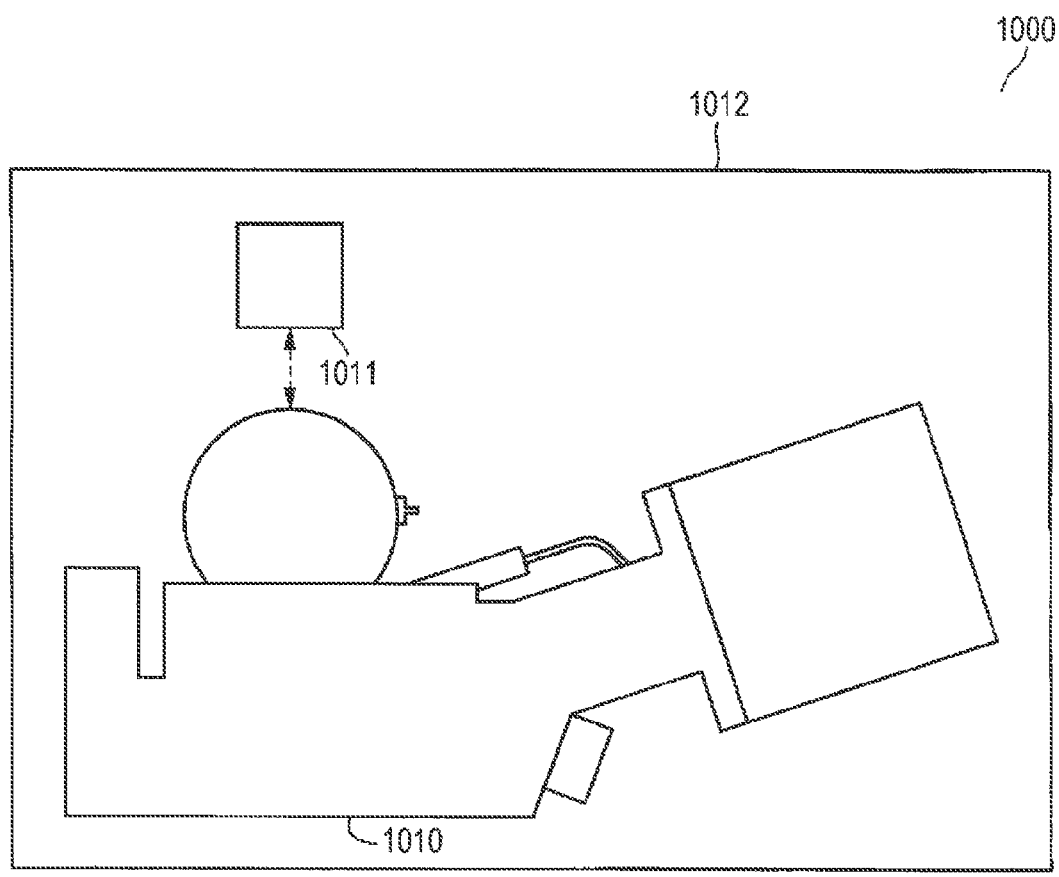
FIG. 1 is a schematic diagram illustrating a gloss colorimeter of a first embodiment.

A schematic diagram of FIG. 1 illustrates a gloss colorimeter of the first embodiment.

A gloss colorimeter 1000 illustrated in FIG. 1 serves as a glossmeter and a spectral colorimeter and measures gloss and spectral reflectance of a sample. A reflection characteristic other than the spectral reflectance may be measured. For example, a color gamut may be measured. That is, the spectral colorimeter function of the gloss colorimeter 1000 may be changed to a function of a reflection characteristic measurement device other than the spectral colorimeter so that the gloss colorimeter 1000 is changed to a surface characteristic measurement device serving as a glossmeter and a reflection characteristic measurement device. For example, the spectral colorimeter function of the gloss colorimeter 1000 may be changed to a color measurement instrument function.

The gloss measurement is performed under a geometry in which an illumination angle and a light receiving angle become 60°. The color measurement is performed under a geometry in which an illumination angle becomes 45° and a light receiving angle becomes 0°. In the gloss measurement, an illumination target face is illuminated by a one-direction illumination. In the color measurement, an illumination target face is illuminated by a circular illumination. The illumination target face is a surface of a sample. Both or any one of the geometry and the illumination may be changed.

A color measurement diameter is manually changed between a standard diameter and a small diameter. A gloss measurement diameter is automatically changed between a standard diameter and a small diameter while being interlocked with a change in color measurement diameter. Accordingly, an appropriate measurement diameter is set for both the gloss measurement and the color measurement.

When the gloss or the reflection characteristic of the surface of the sample is not uniform, the measurement diameter is set to the standard diameter. For example, when a surface decorating process such as embossing is performed on the surface of the sample, the measurement diameter is set to the standard diameter. When the measurement diameter is set to the standard diameter, average gloss information or color measurement information in a relatively wide range is obtained and thus a difference in gloss information or color measurement information caused by a difference in measurement target area is suppressed.

When the sample is small or the surface of the sample is curved, the measurement diameter is set to the small diameter. If the measurement diameter is set to the small diameter when the surface of the sample is curved, the dispersion of the light beam flux of the reflected light is suppressed and thus more light beam flux to be received can be received. For this reason, measurement accuracy is improved. As a small sample, for example, a switch button used in an automobile interior part or a part used in a Smartphone may be exemplified.

A gloss measurement target area is located at the same position as a color measurement target area. Accordingly, gloss information and color measurement information can be correlated with each other and thus working efficiency is improved. The gloss colorimeter 2000 may be used only for the gloss measurement, may be used only for the color measurement, or may be used to continuously perform the gloss measurement and the color measurement.

The gloss colorimeter 1000 includes, as illustrated in FIG. 1, a measurement instrument 1010, a control mechanism (or controller) 1011, a casing 1012, and the like. The measurement instrument 1010 is in charge of the gloss measurement and the color measurement. The control mechanism 1011 controls the measurement instrument 1010. The casing 1012 accommodates the measurement instrument 1010, the control mechanism 1011, and the like.

1.2 Measurement Instrument

Figure 2:
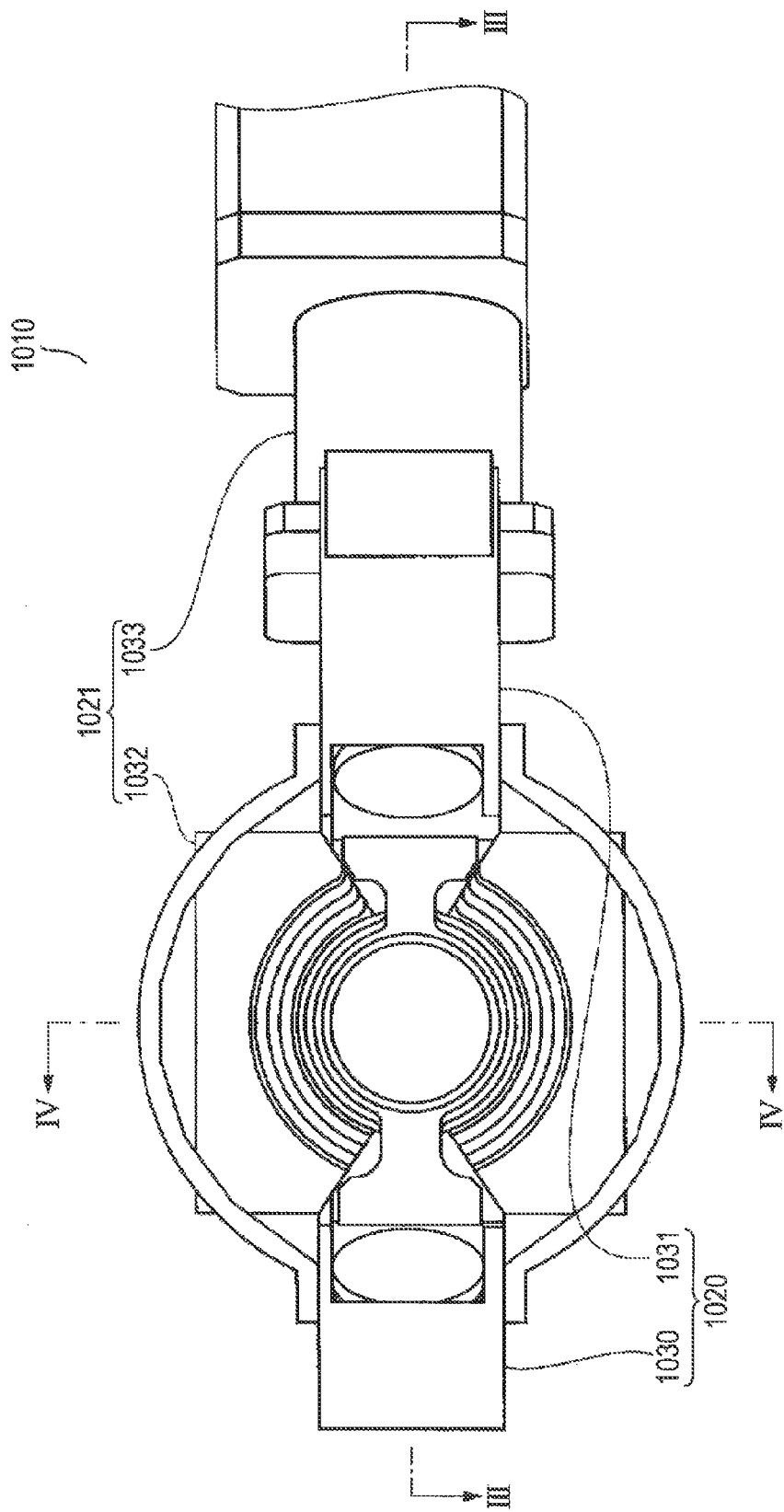
FIG. 2 is a bottom view illustrating a measurement instrument of the first embodiment.
Figure 3:
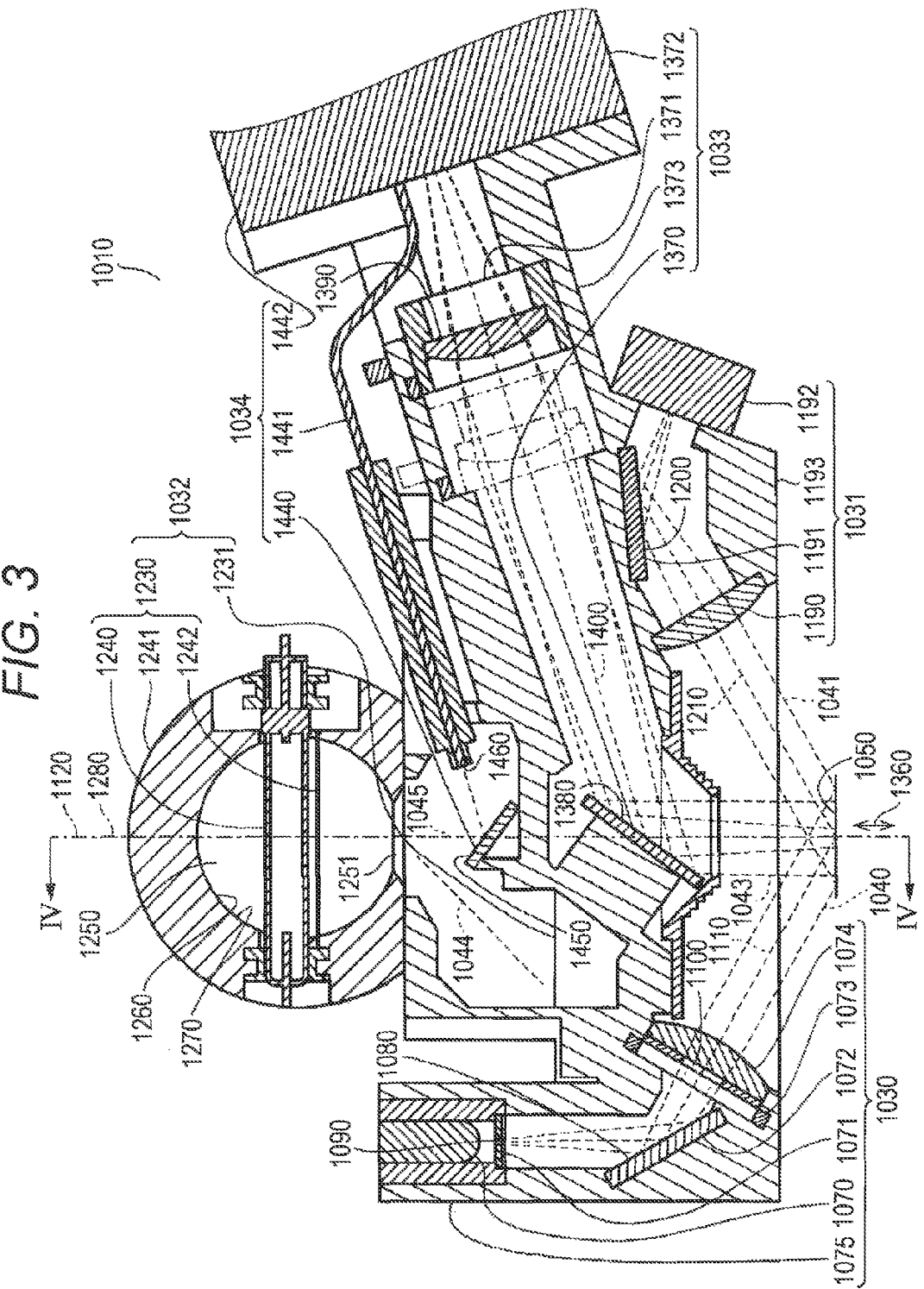
FIG. 3 is a cross-sectional view illustrating the measurement instrument of the first embodiment.
Figure 4:
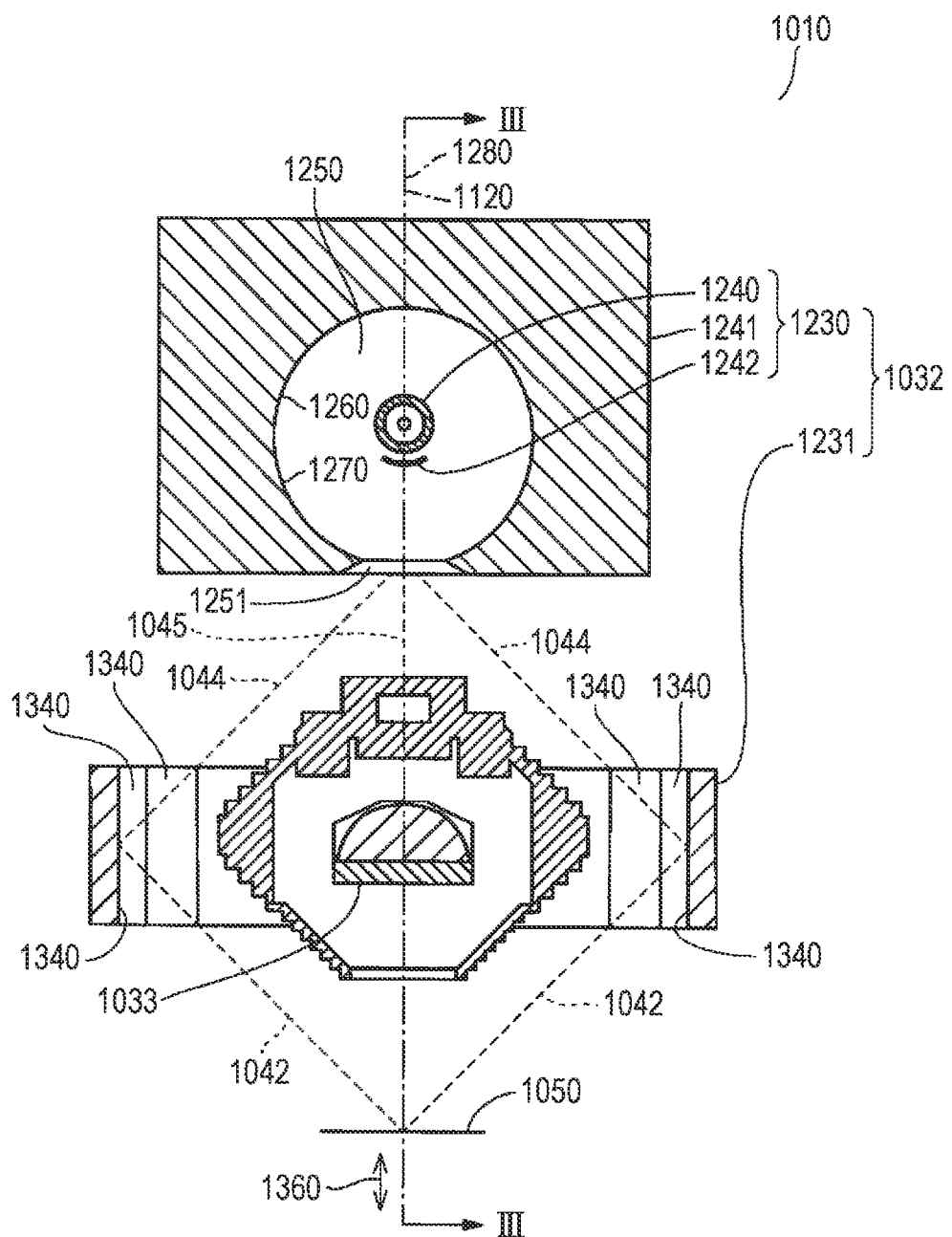
FIG. 4 is a longitudinal sectional view illustrating the measurement instrument of the first embodiment.
Figure 5:
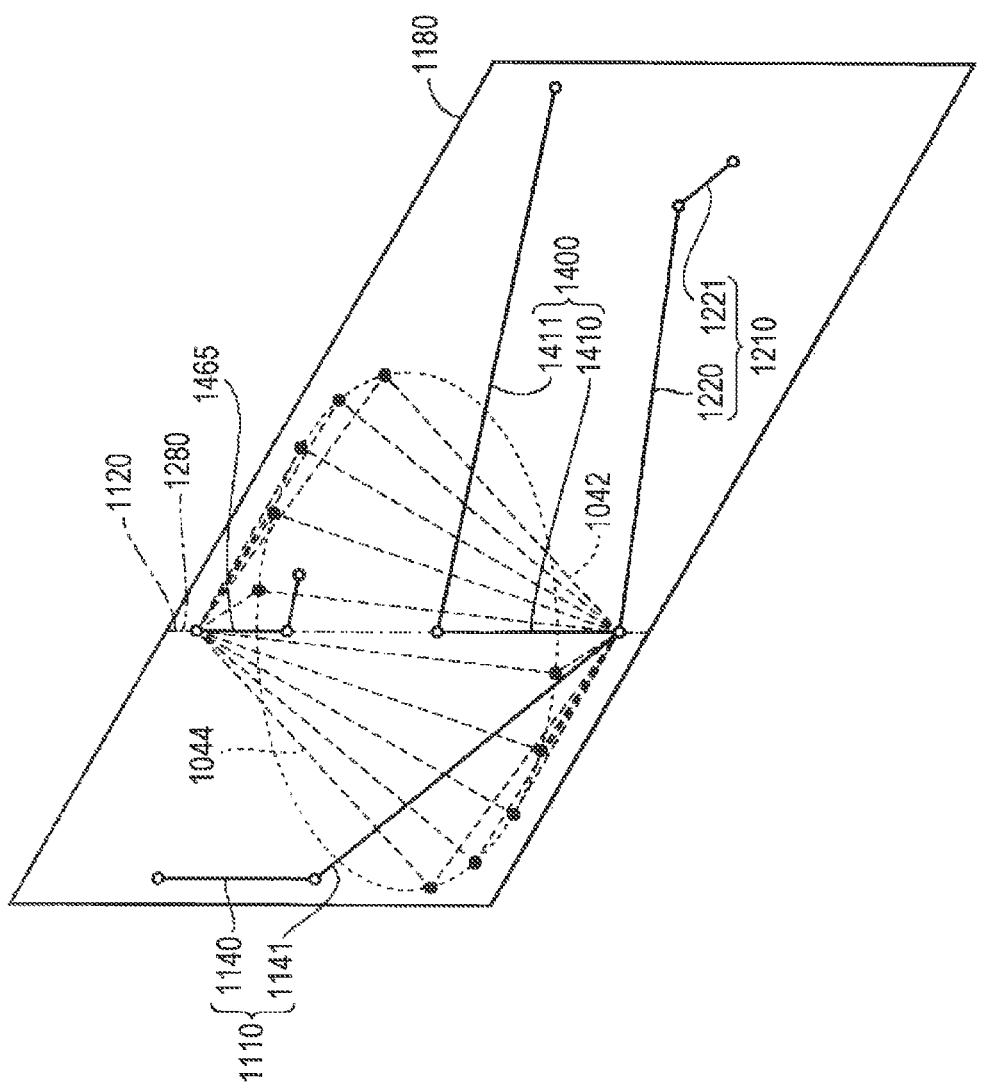
FIG. 5 is a perspective view illustrating an optical axis and the like of the first embodiment.

A schematic diagram of FIG. 2 illustrates a lower face of the measurement instrument. A schematic diagram of FIG. 3 illustrates a cross-sectional face of the measurement instrument. A schematic diagram of FIG. 4 illustrates a longitudinal face of the measurement instrument. A schematic diagram of FIG. 5 is a perspective view illustrating an optical axis and the like.

The measurement instrument 1010 includes, as illustrated in FIG. 2, a gloss measurement instrument 1020, a color measurement instrument 1021, and the like. The gloss measurement instrument 1020 is in charge of the gloss measurement. The color measurement instrument 1021 is in charge of the color measurement. When the spectral colorimeter function is changed to a function of the reflection characteristic measurement device other than the spectral colorimeter, the color measurement instrument 1021 is changed to a reflection characteristic measurement instrument which is in charge of the reflection characteristic measurement other than the color measurement.

The gloss measurement instrument 1020 includes, as illustrated in FIGS. 2 and 3, a gloss measurement illumination mechanism 1030, a gloss measurement light receiving mechanism 1031, and the like. The color measurement instrument 1021 includes, as illustrated in FIGS. 2, 3, and 4, a color measurement illumination mechanism 1032, a color measurement light receiving mechanism 1033, a correction light receiving mechanism 1034, and the like. The gloss measurement illumination mechanism 1030 illuminates an illumination target face 1050 by illumination light 1040. The gloss measurement light receiving mechanism 1031 receives reflected light 1041 and outputs a measurement result for the reflected light 1041. The color measurement illumination mechanism 1032 illuminates an illumination target face 1050 by annular illumination light 1042. The color measurement light receiving mechanism 1033 receives reflected light 1043 and outputs a measurement result for the reflected light 1043. The correction light receiving mechanism 1034 receives light 1045 and outputs a measurement result for the light 1045. The correction light receiving mechanism 1034 may be omitted.

In the measurement instrument 1010, the gloss measurement instrument 1020 and the color measurement instrument 1021 are integrated with each other. The measurement instrument 1010 is accommodated in the casing 1012. Accordingly, the gloss measurement instrument 1020 and the color measurement instrument 1021 coexist in one gloss colorimeter 1000 and thus both the gloss measurement and the color measurement can be performed by one gloss colorimeter 1000. The gloss measurement instrument and the color measurement instrument may be integrated with each other by a different structure. For example, the gloss measurement instrument and the color measurement instrument may be attached to a frame or a casing so that the gloss measurement instrument and the color measurement instrument are integrated with each other through the frame or the casing.

1.3 Gloss Measurement Illumination Mechanism

The gloss measurement illumination mechanism 1030 includes, as illustrated in FIG. 3, a halogen lamp 1070, an aperture plate 1071, a mirror 1072, a gloss measurement diameter changing mechanism 1073, a lens 1074, a barrel 1075, and the like. The gloss measurement illumination mechanism 1030 illuminates an illumination target area of the illumination target face 1050 by the illumination light 1040. The halogen lamp 1070 emits the illumination light 1040. The aperture plate 1071 limits the light beam flux of the illumination light 1040. The mirror 1072 reflects the illumination light 1040. The gloss measurement diameter changing mechanism 1073 changes the gloss measurement diameter. The lens 1074 collimates the illumination light 1040. The barrel 1075 holds the halogen lamp 1070, the aperture plate 1071, the mirror 1072, the gloss measurement diameter changing mechanism 1073, the lens 1074, and the like.

A reflection face 1080 of the mirror 1072 is directed toward a direction between a direction toward the halogen lamp 1070 and a direction toward the illumination target face 1050. A slit-shaped opening 1090 formed in the aperture plate 1071 exists between the halogen lamp 1070 and the reflection face 1080. An oval opening 1100 and the lens 1074 formed in the gloss measurement diameter changing mechanism 1073 exist between the reflection face 1080 and the illumination target face 1050.

The illumination light 1040 advances along an optical axis 1110. The illumination light 1040 is emitted from the halogen lamp 1070, passes through the opening 1090, is reflected by the mirror 1072, passes through the opening 1100, passes through the lens 1074, and is incident to the illumination target face 1050 from a direction of an illumination angle of 60°. The direction of the illumination angle of 60° is a direction which forms an angle of 60° with respect to a normal line 1120 of the illumination target face 1050. When the illumination light 1040 passes through the opening 1090, the light beam flux of the illumination light 1040 is limited. In accordance with the size of the opening 1090, the opening angle of the light beam flux of the illumination light 1040 having passed through the opening 1090 is set. When the illumination light 1040 is reflected by the mirror 1072, the optical axis 1110 is bent. When the illumination light 1040 passes through the opening 1100, the light beam flux of the illumination light 1040 is limited. In accordance with the diameter of the opening 1100, the gloss measurement diameter is set. When the illumination light 1040 passes through the lens 1074, the illumination light 1040 is collimated.

A first section 1140 of the optical axis 1110 illustrated in FIG. 5 is a section from the halogen lamp 1070 to the reflection face 1080 and extends in a direction parallel to the extension direction of the normal line 1120. A second section 1141 of the optical axis 1110 illustrated in FIG. 5 is a section from the reflection face 1080 to the illumination target face 1050 and extends in a direction different from the first section 1140 at an illumination angle of 60°. The optical axis 1110 is bent so that the illumination light 1040 advances along the first section 1140 and the second section 1141. The optical axis 1110 may not be bent.

The halogen lamp 1070 may be replaced by a different light source. For example, the halogen lamp 1070 may be replaced by a light emitting diode or the like. The optical system including the aperture plate 1071, the mirror 1072, and the lens 1074 may be replaced to a different optical system. A light beam flux limiting mechanism in which the aperture plate 1071 is not easily called a plate may be used.

1.4 Gloss Measurement Diameter Changing Mechanism

Figure 6:
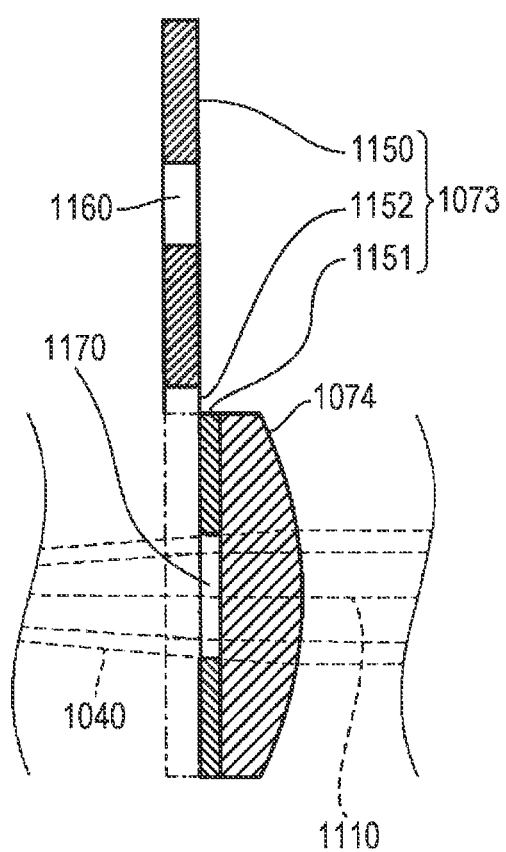
FIG. 6 is a cross-sectional view illustrating a gloss measurement diameter changing mechanism and the like of the first embodiment.

A schematic diagram of FIG. 6 is a cross-sectional view illustrating the gloss measurement diameter changing mechanism and the like. Schematic diagrams of FIGS. 7 and 8 are front views illustrating the gloss measurement diameter changing mechanism and the like.

Figure 7:
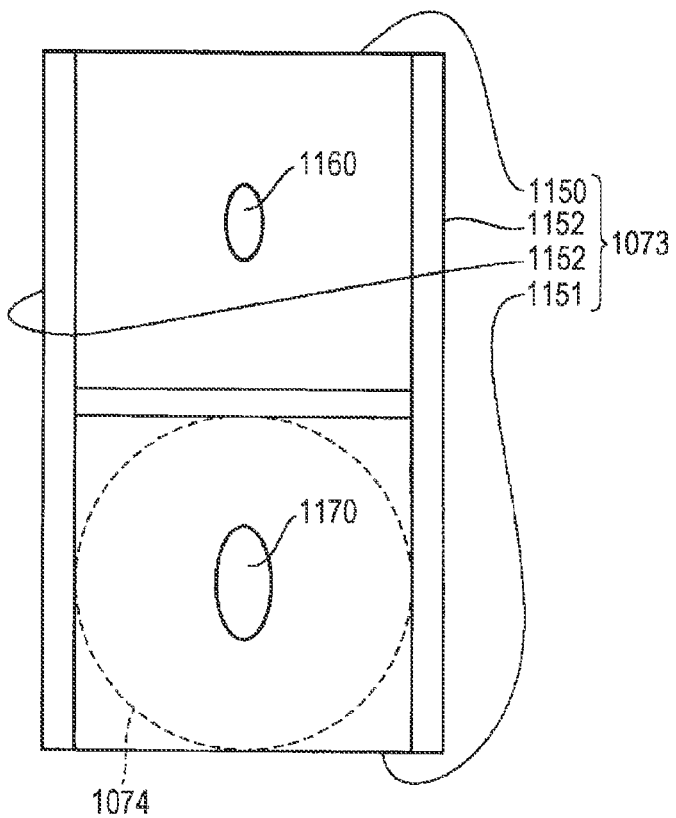
FIG. 7 is a front view illustrating the gloss measurement diameter changing mechanism and the like of the first embodiment.
Figure 8:
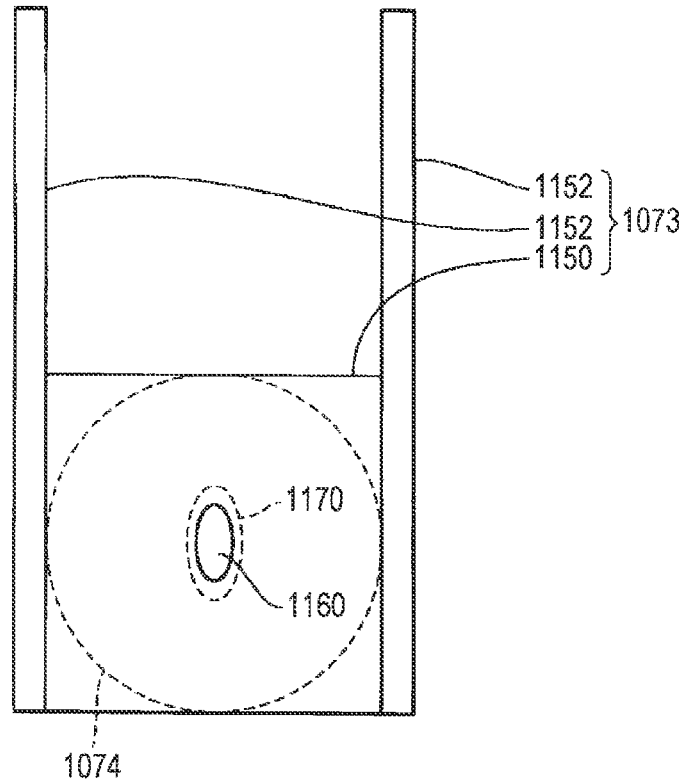
FIG. 8 is a front view illustrating the gloss measurement diameter changing mechanism and the like of the first embodiment.

The gloss measurement diameter changing mechanism 1073 includes, as illustrated in FIGS. 6 to 8, an aperture plate 1150, an aperture plate 1151, a movement mechanism 1152, and the like. The aperture plate 1150 and the aperture plate 1151 limit the light beam flux of the illumination light 1040. The movement mechanism 1152 moves the aperture plate 1150.

The aperture plate 1150 is provided with an opening 1160. The aperture plate 1151 is provided with an opening 1170. A diameter of the opening 1160 is smaller than that of the opening 1170. A light beam flux limiting mechanism having a shape in which both or any one of the aperture plate 1150 and the aperture plate 1151 is not easily called a plate may be used. The aperture plate 1150 is adjacent to the aperture plate 1151 and limits the light beam flux of the illumination light 1040 at the substantially same position as the aperture plate 1151. The aperture plate 1150 and the aperture plate 1151 are perpendicular to the optical axis 1110.

The aperture plate 1150 is moved by the movement mechanism 1152 to be located at the outside of the optical path of the illumination light 1040 as indicated by the solid line of FIG. 6 and illustrated in FIG. 7 or to be located onto the optical path of the illumination light 1040 as indicated by the one-dotted dash line of FIG. 6 or illustrated in FIG. 8. The aperture plate 1151 is fixed on the optical path of the illumination light 1040. The movement mechanism 1152 generates a force of moving the aperture plate 1150 and transmits the force of moving the aperture plate 1150 to the aperture plate 1150. The force of moving the aperture plate 1150 is generated by an electromagnetic motor, an electromagnetic actuator, a piezoelectric actuator, or the like.

When the aperture plate 1150 is located out of the optical path of the illumination light 1040, the aperture plate 1151 overlaps the lens 1074 when viewed from the extension direction of the optical axis 1110 and the illumination light 1040 passing through the gloss measurement diameter changing mechanism 1073 passes through the opening 1170. In this case, the opening 1170 forms the opening 1100 through which the illumination light 1040 passes and the diameter of the opening 1100 is determined by the diameter of the opening 1170.

When the aperture plate 1150 is located on the optical path of the illumination light 1040, the aperture plate 1150 and the aperture plate 1151 overlap the lens 1074 when viewed from the extension direction of the optical axis 1110 and the illumination light 1040 passing through the gloss measurement diameter changing mechanism 1073 passes through the opening 1160 and the opening 1170. In this case, the opening 1160 and the opening 1170 form the opening 1100 through which the illumination light 1040 passes and the diameter of the opening 1100 is determined by the diameter of the relatively small opening 1160.

The gloss measurement diameter changing mechanism 1073 changes the diameter of the opening 1100 in two levels by inserting the aperture plate 1150 into the optical path of the illumination light 1040 or extracting the aperture plate from the optical path of the illumination light 1040. The gloss measurement diameter changing mechanism 1073 may change the diameter of the opening 1100 in three or more levels. The gloss measurement diameter changing mechanism 1073 may continuously change the diameter of the opening 1100. For example, the diameter of the opening 1100 may be continuously changed by a diaphragm aperture.

When the diameter of the opening 1100 is changed, an opening angle of the light beam flux of the illumination light 1040 having passed through the opening 1100 is changed so that the diameter of the gloss measurement illumination target area is changed. When the diameter of the gloss measurement illumination target area is changed, the gloss measurement diameter is changed. When the diameter of the opening 1100 is determined by the diameter of the opening 1170, the diameter of the gloss measurement illumination target area becomes the standard diameter and the gloss measurement diameter becomes the standard diameter. When the size of the opening 1100 is determined by the size of the opening 1160, the diameter of the gloss measurement illumination target area becomes the small diameter and the gloss measurement diameter becomes the small diameter. The diameter of the illumination target area may be changed in accordance with a method other than a change in diameter of the opening 1100. The gloss measurement diameter may be changed in accordance with a method other than a change in diameter of the gloss measurement illumination target area.

The opening 1160 and the opening 1170 have an oval shape when viewed from the extension direction of the optical axis 1110. A short axis of the oval is included in a plane 1180 including the optical axis 1110 and the normal line 1120 of the illumination target face 1050. A long axis of the oval is perpendicular to the plane 1180. When the opening 1160 and the opening 1170 have an oval shape, the gloss measurement illumination target area may have a circular shape. The shapes of the opening 1160 and the opening 1170 may be changed. For example, the opening 1160 and the opening 1170 may have circular or rectangular shape when viewed from the extension direction of the optical axis 1111.

In the color measurement instrument 1021 having a geometry in which an illumination angle based on JIS-Z8722 is 45° and a light receiving angle is 0°, the light receiving target area of the color measurement is circular in many cases. For this reason, when the gloss measurement illumination target area is circular, the shape of the gloss measurement illumination target area can match the shape of the light receiving target area of the color measurement and the shape of the gloss measurement target area can match the shape of the color measurement target area so that the gloss measurement target area can match the color measurement target area. On the contrary, when the opening 1160 and the opening 1170 are circular, the illumination light 1040 is incident to the illumination target face 1050 from a direction forming an angle of 60° with respect to the normal line 1120 of the illumination target face 1050. For this reason, the gloss measurement illumination target area has an oval shape in which a length of a long axis is two times a length of a short axis. Accordingly, the gloss measurement target area may match the color measurement target area.

The diameter of the gloss measurement illumination target area is changed in accordance with a change in diameter of the opening 1100 through which the illumination light 1040 passes and the gloss measurement diameter is changed in accordance with a change in diameter of the gloss measurement illumination target area. More generally, the size of the gloss measurement illumination target area is changed in accordance with a change in size of the opening 1100 through which the illumination light 1040 passes and the size of the gloss measurement target area is changed in accordance with a change in size of the gloss measurement illumination target area. This general description is applied to a case where the diameter of the opening 1100 is not easily defined.

1.5 Gloss Measurement Light Receiving Mechanism

The gloss measurement light receiving mechanism 1031 includes, as illustrated in FIG. 3, a lens 1190, a mirror 1191, a light amount measurement instrument 1192, a barrel 1193, and the like. The lens 1190 converges the light beam flux of the reflected light 1041. The mirror 1191 reflects the reflected light 1041. The light amount measurement instrument 1192 outputs a signal depending on the light amount of the reflected light 1041.

The reflection face 1200 of the mirror 1191 is directed toward a direction between a direction toward the illumination target face 1050 and a direction toward the light amount measurement instrument 1192. The lens 1190 exists between the illumination target face 1050 and the reflection face 1200.

The reflected light 1041 advances along an optical axis 1210. The reflected light 1041 is generated by the regular reflection of the illumination light 1040 on the illumination target face 1050, is emitted from the illumination target face 1050 in a direction of a light receiving angle of 60°, passes through the lens 1190, is reflected by the mirror 1191, and is received by the light amount measurement instrument 1192. The direction of the light receiving angle of 60° is a direction which forms an angle of 60° with respect to the normal line 1120 of the illumination target face 1050. The light amount measurement instrument 1192 outputs a signal depending on the light amount of the reflected light 1041. A signal which is output from the light amount measurement instrument 1192 becomes a measurement result for the reflected light 1041. When the reflected light 1041 passes through the lens 1190, the light beam flux of the reflected light 1041 is converged. When the reflected light 1041 is reflected by the mirror 1191, the optical axis 1210 is bent.

A first section 1220 of the optical axis 1210 illustrated in FIG. 5 is a section from the illumination target face 1050 to the reflection face 1200 and extends in the direction of the light receiving angle of 60°. A second section 1221 of the optical axis 1210 illustrated in FIG. 5 is a section front the reflection face 1200 to the light amount measurement instrument 1192 and extends in a direction different from the extension direction of the first section 1220. The optical axis 1210 is bent so that the reflected light 1041 advances along the first section 1220 and the second section 1221. The optical axis 1210 may not be bent.

The optical system including the lens 1190 and the mirror 1191 may be replaced by a different optical system.

1.6 Color Measurement Illumination Mechanism

The color measurement illumination mechanism 1032 includes, as illustrated in FIGS. 3 and 4, a light emitting mechanism 1230, a reflection mechanism 1231, and the like.

The light emitting mechanism 1230 emits the light 1044, the light 1045, and the like. The reflection mechanism 1231 sets the light 1044 as the annular illumination light 1042. The color measurement illumination mechanism 1032 may be replaced by a different illumination mechanism.

1.7 Light Emitting Mechanism

The light emitting mechanism 1230 includes, as illustrated in FIGS. 3 and 4, a straight tube type xenon lamp 1240, an integrating sphere 1241, a baffle 1242, and the like. The straight tube type xenon lamp 1240 emits light. The integrating sphere 1241 is used to obtain uniform light. The baffle 1242 is used to suppress non-uniform emission of light.

A spherical space 1250 which is formed in the integrating sphere 1241 is defined by the inner face 1260 of the integrating sphere 1241. A round-hole-shaped light emitting opening 1251 which is formed in the integrating sphere 1241 is used to communicate the space 1250 and the outside of the integrating sphere 1241 with each other.

The inner face 1260 includes a dispersion reflection face 1270. The entire inner face 1260 becomes the dispersion reflection face 1270, but the inner face 1260 may be a slight face other than the dispersion reflection face 1270.

When the straight tube type xenon lamp 1240 emits light, the light sequentially advances through the space 1250 and the light emitting opening 1251 so that the light is finally emitted to the outside of the integrating sphere 1241. While the light advances through the space 1250, the light is dispersed and reflected by the dispersion reflection face 1270 at least once. While the light advances through the space 1250, most of the light is repeatedly dispersed and reflected by the dispersion reflection face 1270. When the light is dispersed and reflected by the dispersion reflection face 1270 and is emitted from the light emitting opening 1251, the light is uniformly emitted from the light emitting mechanism 1230. Accordingly, the light emitting mechanism 1230 substantially has a vertical light distribution characteristic according to Lambert's cosine law. When the light emitting mechanism 1230 has a vertical light distribution characteristic according to Lambert's cosine law, the intensity of the light emitted in a direction forming an angle θ with respect to a reference axis 1280 is proportional to a cosine θ of the angle θ.

A main part of the straight tube type xenon lamp 1240 and a main part of the baffle 1242 exist in the space 1250. The baffle 1242 exists between the straight tube type xenon lamp 1240 and the light emitting opening 1251. The light beam which is directly directed from the straight tube type xenon lamp 1240 toward the light emitting opening 1251 is shielded by the baffle 1242. Accordingly, it is possible to suppress the light emitted from the straight tube type xenon lamp 1240 from being emitted from the light emitting opening 1251 without the dispersion and the reflection by the dispersion reflection face 1270. As a result, stray light is suppressed and color measurement accuracy is improved.

The light emitting mechanism 1230 may be changed to a different light emitting mechanism.

1.8 Reflection Mechanism

Figure 9:
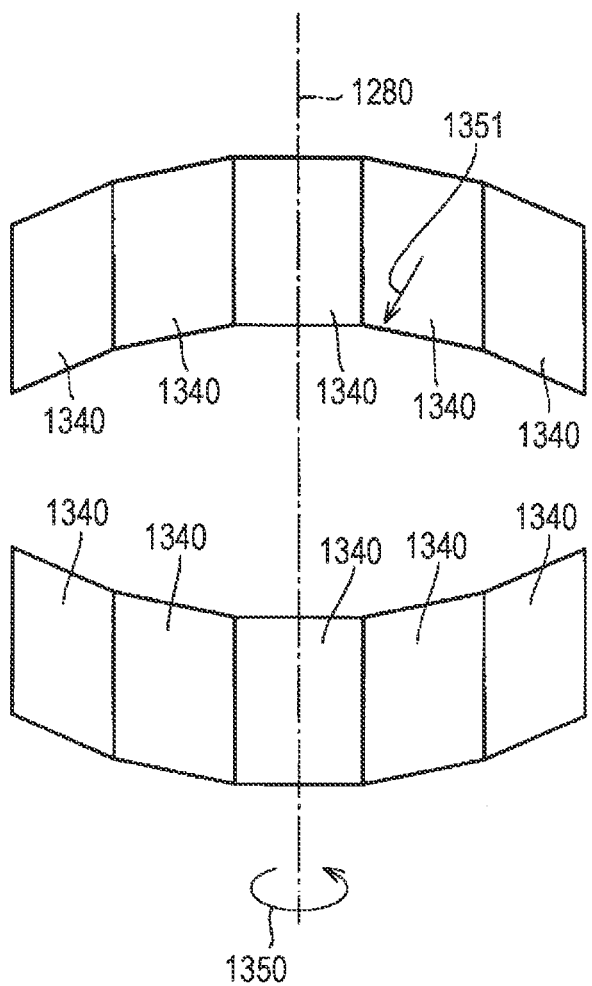
FIG. 9 is a perspective view illustrating an arrangement of a planar reflection face of the first embodiment.

A schematic diagram of FIG. 9 is a perspective view illustrating an arrangement of planar reflection faces.

The reflection mechanism 1231 illustrated in FIGS. 3 and 4 includes, as illustrated in FIG. 9, ten planar reflection faces 1340. Each of the ten planar reflection faces 1340 is a mirror face and reflects the light 1044. Ten planar reflection faces 1340 are arranged about the reference axis 1280 to be distributed in a circumferential direction 1350 surrounding the reference axis 1280. Ten planar reflection faces 1340 are directed toward an inner radial side 1351 which becomes closer to the reference axis 1280. Ten planar reflection faces 1340 are arranged so that the light 1044 becomes incident light and the reflected light becomes the annular illumination light 1042. The annular illumination light 1042 is incident to the illumination target face 1050 from a direction of an illumination angle of 45°. The direction of the illumination angle of 45° is a direction which forms an angle of 45° with respect to the normal line 1120 of the illumination target face 1050.

When the light 1044 emitted from the light emitting opening 1251 in a direction forming an angle of 45° with respect to the reference axis 1280 becomes illumination light which is incident to the illumination target face 1050 from a direction of the illumination angle of 45° according to the vertical light distribution characteristic of the light emitting mechanism 1230 based on Lambert's cosine law, the illumination is not largely changed even when the illumination target face 1050 moves from the reference position in the axial direction 1360 and thus color measurement stability is improved.

When two or more planar reflection faces 1340 are arranged to be distributed in the circumferential direction 1350, the illumination target face 1050 is illuminated from two or more directions distributed in the circumferential direction 1350. When the illumination target face 1050 is illuminated from two or more directions distributed in the circumferential direction 1350, the reflected light 1043 is not largely changed by the direction of the illumination target face 1050 even when the illumination target face 1050 has an anisotropic reflection characteristic and thus color measurement stability is improved.

A color measurement illumination target area illuminated by the annular illumination light 1042 overlaps a gloss measurement illumination target area illuminated by the illumination light 1040. The position of the color measurement illumination target area illuminated by the annular illumination light 1042 matches the position of the gloss measurement illumination target area illuminated by the illumination light 1040. Accordingly, the position of the gloss measurement target area can be indicated by the annular illumination light 1042 for the color measurement in the gloss measurement and the position of the color measurement target area can be indicated by the illumination light 1040 for the gloss measurement in the color measurement. When the position of the gloss measurement target area is indicated by the annular illumination light 1042, the straight tube type xenon lamp 1240 is replaced by a light source continuously emitting light.

Ten planar reflection faces 1340 may be changed to nine or less or eleven or more planar reflection faces. Ten planar reflection faces 1340 may be changed to a cylindrical reflection face, a rotary oval reflection face, or the like.

1.9 Color Measurement Light Receiving Mechanism

The color measurement light receiving mechanism 1033 includes, as illustrated in FIG. 3, a mirror 1370, a color measurement diameter changing mechanism 1371, a spectral measurement instrument 1372, a barrel 1373, and the like. The color measurement light receiving mechanism 1033 receives the reflected light 1043 generated by a reflection of the annular illumination light 1042 on the light receiving target area of the illumination target face 1050. The mirror 1370 reflects the reflected light 1043. The color measurement diameter changing mechanism 1371 chances the color measurement diameter. The spectral measurement instrument 1372 outputs a signal depending on the light amount of each wavelength component of the reflected light 1043. The barrel 1373 holds the mirror 1370, the color measurement diameter changing mechanism 1371, and the like. The barrel 1373 is integrated with the barrel 1075 and the barrel 1193 to form a barrel assembly.

The mirror 1370 exists on the normal line 1120 of the illumination target face 1050. A reflection face 1380 of the mirror 1370 is directed toward a direction between a direction toward the illumination target face 1050 and a direction toward the spectral measurement instrument 1372. A lens 1390 of the color measurement diameter changing mechanism 1371 exists between the reflection face 1380 and the spectral measurement instrument 1372.

The reflected light 1043 advances along an optical axis 1400. The reflected light 1043 is generated by a reflection of the annular illumination light 1042 on the illumination target face 1050, is emitted from the illumination target face 1050 in a direction of a light receiving angle of 0°, is reflected by the mirror 1370, passes through the lens 1390, and is received by the spectral measurement instrument 1372. The direction of the light receiving angle of 0° is a direction that forms an angle of 0° with respect to the normal line 1120 of the illumination target face 1050. The spectral measurement instrument 1372 outputs a signal depending on the light amount of each wavelength component of the reflected light 1043. A signal output from the spectral measurement instrument 1372 becomes a measurement result for the reflected light 1043. When the reflected light 1043 is reflected by the mirror 1370, the optical axis 1400 is bent. When the reflected light 1043 passes through the lens 1390, the light beam flux of the reflected light 1043 is converged.

A first section 1410 of the optical axis 1400 illustrated in FIG. 5 is a section from the illumination target face 1050 to the reflection face 1380 and extends in the direction of the light receiving angle of 0°. A second section 1411 of the optical axis 1400 illustrated in FIG. 5 is a section from the reflection face 1380 to the spectral measurement instrument 1372 and extends in a direction different from the extension direction of the first section 1410. The optical axis 1400 is bent so that the reflected light 1043 advances along the first section 1410 and the second section 1411. The optical axis 1400 may not be bent.

The optical system including the mirror 1370 may be replaced by a different optical system. When the spectral colorimeter function of the gloss colorimeter 1000 is changed to the color measurement instrument function, the spectral measurement instrument 1372 may be replaced by a mechanism that directly reads tristimulus values.

1.10 Color Measurement Diameter Changing Mechanism

Figure 10:
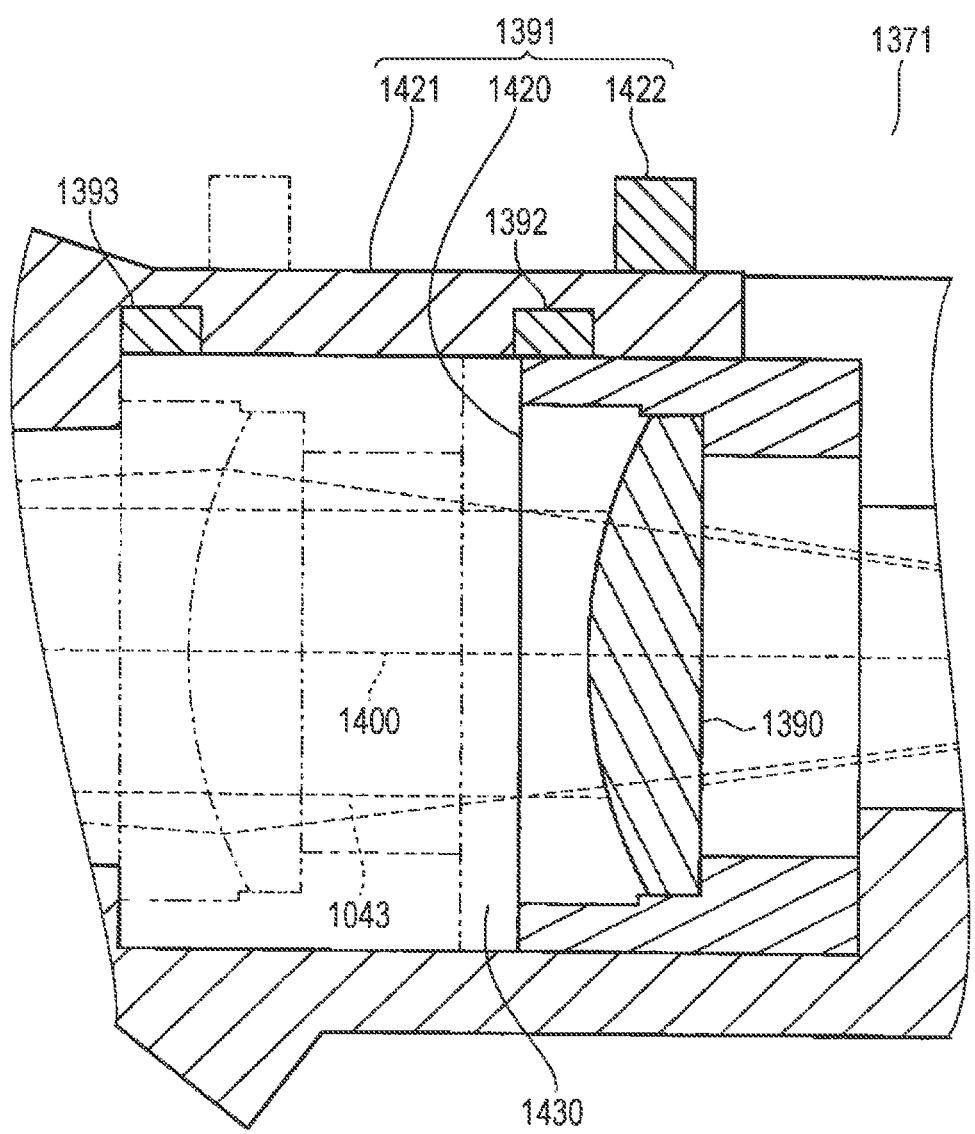
FIG. 10 is a cross-sectional view illustrating a color measurement diameter changing mechanism and the like of the first embodiment.

A schematic diagram of FIG. 10 is a cross-section illustrating the color measurement diameter changing mechanism and the like.

The color measurement diameter changing mechanism 1371 includes, as illustrated in FIG. 10, the lens 1390, a parallel movement mechanism 1391, a limit switch 1392, a limit switch 1393, and the like. The lens 1390 converges the light beam flux of the reflected light 1043. The parallel movement mechanism 1391 moves the lens 1390 in parallel. The limit switch 1392 and the limit switch 1393 detect the position of the lens holder 1420.

The parallel movement mechanism 1391 includes the lens holder 1420, a guide cylinder 1421, a knob 1422, and the like. The lens holder 1420 holds the lens 1390. The guide cylinder 1421 guides the lens holder 1420. The knob 1422 transmits an applied force to the lens holder 1420. The knob 1422 may be replaced by a different operation member. A driving mechanism which generates a part or the entirety of a force transmitted to the lens holder 1420 may be provided.

The lens holder 1420 is inserted into a guide hole 1430 formed in the guide cylinder 1421 and is slidable in the extension direction of the guide hole 1430. The extension direction of the guide hole 1430 matches the extension direction of the optical axis 1400. Accordingly, the movement direction of the lens 1390 is regulated in the extension direction of the optical axis 1400 and the lens 1390 is guided in the extension direction of the optical axis 1400. When a force is applied to the knob 1422, the applied force is transmitted to the lens holder 1420 so that the lens 1390 and the lens holder 1420 move together in parallel to the optical axis 1400.

The lens 1390 is moved in parallel by the parallel movement mechanism 1391 so as to be near the spectral measurement instrument 1372 as indicated by the solid line of FIG. 10 or near the illumination target face 1050 as indicated by the two-dotted dash line of FIG. 10.

When the parallel movement mechanism 1391 moves the lens 1390 in parallel along the optical axis 1400, the position of the lens 1390 is changed in two levels. The parallel movement mechanism 1391 may change the position of the lens 1390 in three or more levels. The parallel movement mechanism 1391 may continuously change the position of the lens 1390.

When the lens 1390 is moved along the optical axis 1400 in parallel, the opening angle of the light beam flux of the reflected light 1043 to pass through the lens 1390 is changed and the diameter of the light receiving target area in the color measurement is changed. When the diameter of the light receiving target area of the color measurement is changed, the color measurement diameter is changed.

When the lens 1390 is near the spectral measurement instrument 1372, the diameter of the light receiving target area of the color measurement becomes the standard diameter and the color measurement diameter becomes the standard diameter. When the lens 1390 is near the illumination target face 1050, the diameter of the light receiving target area of the color measurement becomes the small diameter and the color measurement diameter becomes the small diameter.

The limit switch 1392 detects a state where the lens holder 1420 is near the spectral measurement instrument 1372. The limit switch 1393 detects a state where the lens holder 1420 is near the illumination target face 1050. When the lens holder 1420 is near the spectral measurement instrument 1372, the lens 1390 is near the spectral measurement instrument 1372 so that the color measurement diameter becomes the standard diameter. Then, when the lens holder 1420 is near the illumination target face 1050, the lens 1390 is near the illumination target face 1050 so that the color measurement diameter becomes the small diameter. For this reason, the color measurement diameter is determined by the position of the lens holder 1420 and the limit switch 1392 and the limit switch 1393 output a detection result for the position of the lens holder 1420 for determining the color measurement diameter. A position of a constituent other than the lens holder 1420 may be detected. For example, the position of the lens 1390, the knob 1422, or the like may be detected. The position may be detected by a detection mechanism other than the limit switch 1392 and the limit switch 1393. For example, the position may be detected by a laser displacement gauge.

The color measurement diameter is changed in accordance with a change in diameter of the light receiving target area of the color measurement. More generally, the size of the color measurement target area is changed in accordance with a change in size of the light receiving target area of the color measurement. This general description is applied to a case where the light receiving target area of the color measurement has a shape in which a diameter is not easily defined.

1.11 Correction Light Receiving Mechanism

The correction light receiving mechanism 1034 includes, as illustrated in FIG. 3, a mirror 1440, an optical fiber 1441, a spectral measurement instrument 1442, and the like. The spectral measurement instrument 1442 is common to the spectral measurement instrument 1372.

The light 1045 advances along the optical axis 1465. The light 1045 is emitted from the light emitting opening 1251 in a direction forming an angle of 0° with respect to the reference axis 1280, is reflected by the mirror 1440, is guided to the optical fiber 1441, and is received by the spectral measurement instrument 1442. The spectral measurement instrument 1442 outputs a signal depending on the light amount of each wavelength component of the light 1045.

1.12 Control Mechanism

Figure 11:
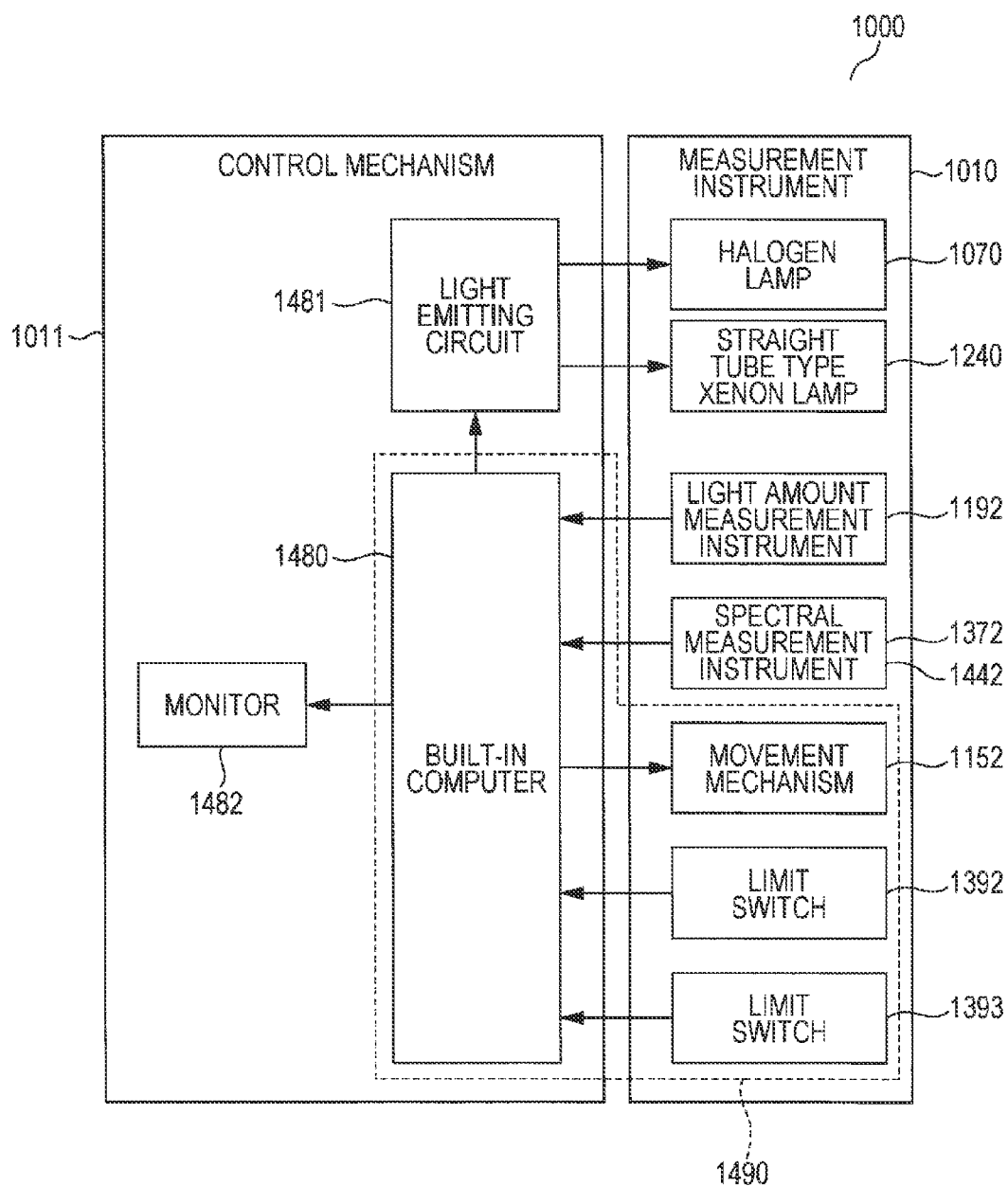
FIG. 11 is a block diagram illustrating the gloss colorimeter of the first embodiment.

A block diagram of FIG. 11 illustrates a gloss colorimeter.

The control mechanism 1011 includes, as illustrated in FIG. 11, a built-in computer 1480, a light emitting circuit 1481, a monitor 1482, and the like.

The built-in computer 1480 controls the light emitting circuit 1481, the monitor 1482, the measurement instrument 1010, and the like by performing an installed firmware so that a process is performed in accordance with the firmware. A part or the entirety of the process performed by the built-in computer 1480 may be performed by hardware not performing a program. The light emitting circuit 1481 supplies electric power to the halogen lamp 1070 and the straight tube type xenon lamp 1240. The monitor 1482 displays information.

The built-in computer 1480 controls an illumination of the illumination light 1040 by controlling the supply of the electric power from the light emitting circuit 1481 to the halogen lamp 1070 and controls an illumination of the annular illumination light 1042 by controlling the supply of the electric power from the light emitting circuit 1481 to the straight tube type xenon lamp 1240. The built-in computer 1480 acquires a measurement result from the light amount measurement instrument 1192 and acquires a measurement result from the spectral measurement instrument 1372 and the spectral measurement instrument 1442. The built-in computer 1480 obtains gloss information from the measurement result acquired from the light amount measurement instrument 1192 and obtains color measurement information from the measurement result acquired from the spectral measurement instrument 1372. The built-in computer 1480 performs a correction reflecting the measurement result acquired from the spectral measurement instrument 1442 when the color measurement information is obtained. Accordingly, it is possible to reduce an influence of a change in light emitted from the light emitting mechanism 1230 with respect to the color measurement information. The gloss information includes gloss and the like. The color measurement information includes a spectrum, a color gamut, and the like. The built-in computer 1480 displays the gloss information and the color measurement information obtained in this way on the monitor 1482.

The built-in computer 1480 acquires a detection result from the limit switch 1392 and the limit switch 1393. When the lens holder 1420 moves near the spectral measurement instrument 1372, the built-in computer 1480 moves the aperture plate 1150 to the outside of the optical path of the illumination light 1040 by the movement mechanism 1152. When the lens holder 1420 moves near the illumination target face 1050, the built-in computer 1480 moves the aperture plate 1150 onto the optical path of the illumination light 1040 by the movement mechanism 1152. Accordingly, an interlocking mechanism 1490 changing the gloss measurement diameter by the gloss measurement instrument 1020 in accordance with a detection result of the limit switch 1392 and the limit switch 1393 so that the gloss measurement diameter is changed in synchronization with a change in color measurement diameter is formed. When the color measurement diameter is changed to the standard diameter, the gloss measurement diameter is changed to the standard diameter in synchronization with a change in color measurement diameter. When the color measurement diameter is changed to the small diameter, the gloss measurement diameter is changed to the small diameter in synchronization with a change in color measurement diameter. The gloss measurement diameter matches the color measurement diameter in synchronization with the color measurement diameter.

According to the interlocking mechanism 1490, since there is no need to cause the gloss measurement diameter to match the color measurement diameter, it is possible to prevent an erroneous measurement caused when the gloss measurement diameter does not match the color measurement diameter. Accordingly, the gloss measurement target area and the color measurement target area are appropriately set. Further, since an operation necessary for causing the gloss measurement diameter to match the color measurement diameter is reduced, measurement efficiency is improved.

When the gloss measurement target area is located at the same position as the color measurement target area, a correction reflecting the measurement result acquired from the spectral measurement instrument 1372 may be performed when the gloss information is obtained from the measurement result acquired by the light amount measurement instrument 1192. By this correction, an influence of the color of the illumination target face 1050 with respect to the gloss information is reduced. For example, when the color of the illumination target face 1050 is white, the inner dispersion light becomes stronger compared to a case where the color of the illumination target face 1050 is black. Accordingly, there is a strong tendency that gloss which is stronger than real gloss is measured. By the reflection of the measurement result acquired from the spectral measurement instrument 1372, a difference from real gloss is suppressed.

1.13 Measurement Sequence

When the gloss measurement and the color measurement are continuously performed, the built-in computer 1480 performs the color measurement by the color measurement instrument 1021, acquires a measurement result from the color measurement instrument 1021, and derives color measurement information from the measurement result. The built-in computer 1480 performs the gloss measurement by the gloss measurement instrument 1020 while driving color measurement information from the measurement result.

In the gloss measurement, the reflected light 1041 is received by a single-cell sensor having light sensitivity based on JIS-Z8741 and a single signal is output in response to the light amount of the reflected light 1041. On the contrary, in the color measurement, multiple signals are output in response to the light amount of the wavelength component of the reflected light 1043. For this reason, a time necessary to derive the color measurement information is longer than a time necessary for a process of deriving the gloss information.

When the gloss measurement instrument 1020 performs the gloss measurement while deriving the color measurement information, a time taken for the completion of the gloss measurement and the color measurement is shortened and thus measurement efficiency is improved.

2 Second Embodiment

A second embodiment relates to a gloss measurement diameter changing mechanism to be used instead of the gloss measurement diameter changing mechanism of the first embodiment. A technology used in the other embodiment may be used in the second embodiment.

Figure 12:
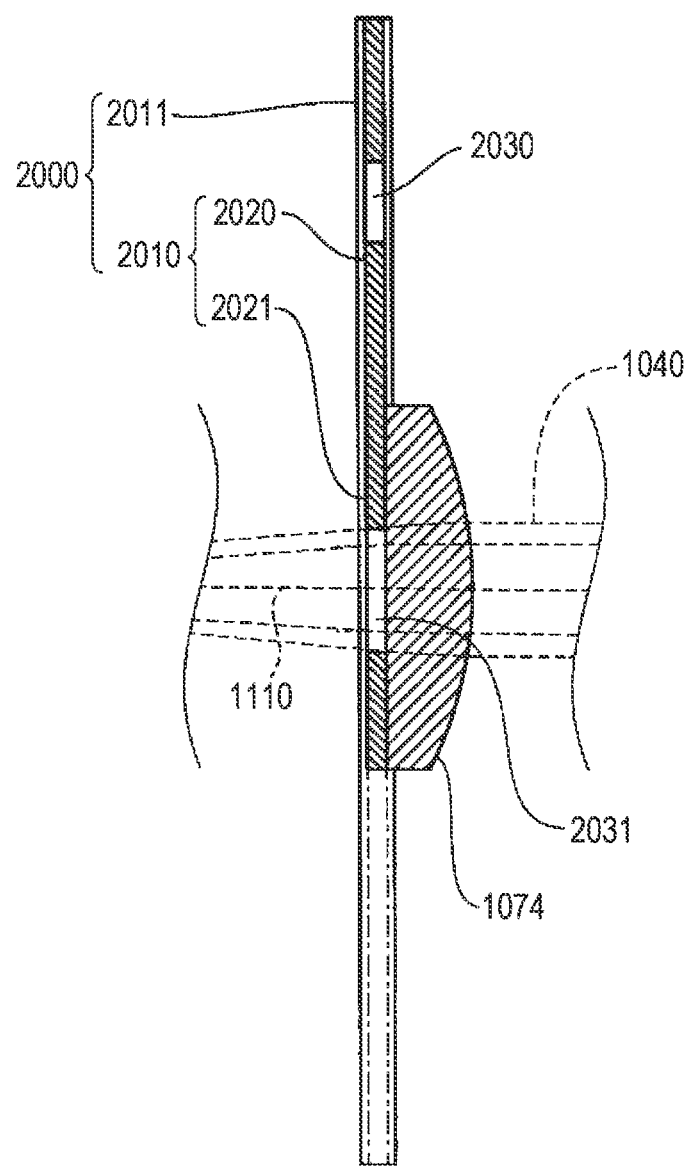
FIG. 12 is a cross-sectional view illustrating a gloss measurement diameter changing mechanism and the like of a second embodiment.

A schematic diagram of FIG. 12 is a cross-sectional view illustrating the gloss measurement diameter changing mechanism and the like. Schematic diagrams of FIGS. 13 and 14 are front views illustrating the gloss measurement diameter changing mechanism and the like.

Figure 13:
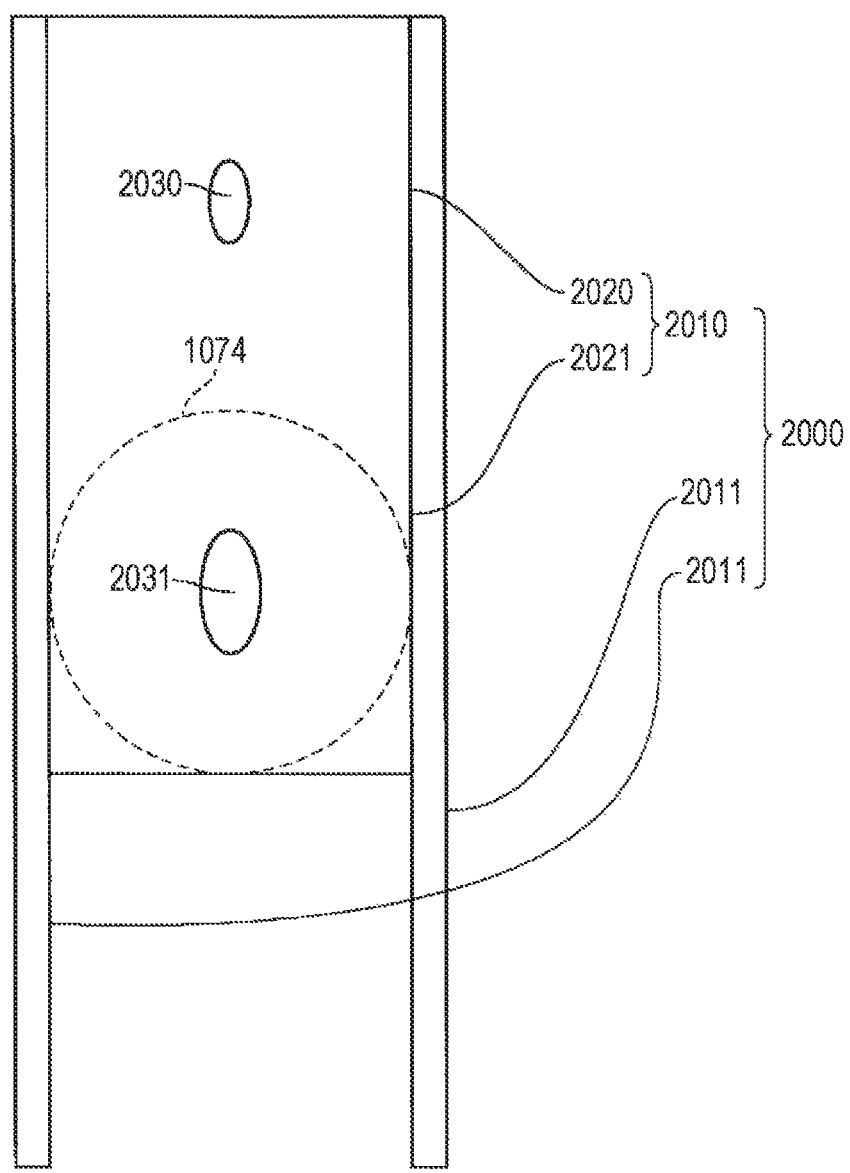
FIG. 13 is a front view illustrating the gloss measurement diameter changing mechanism and the like of the second embodiment.
Figure 14:
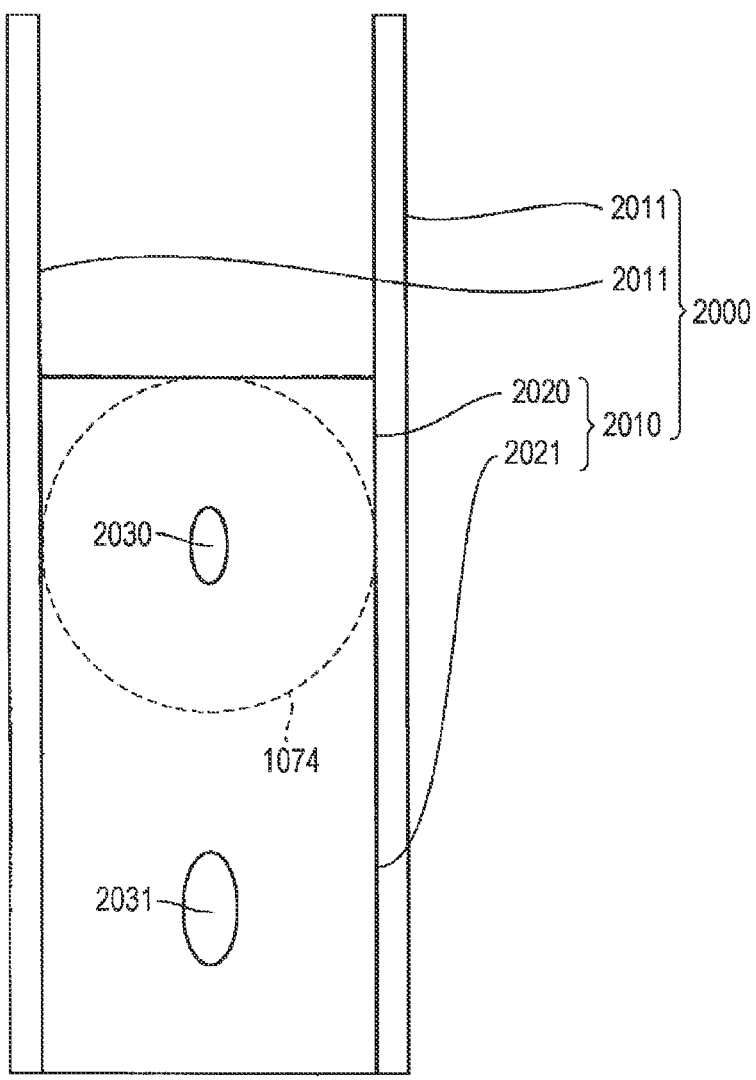
FIG. 14 is a front view illustrating the gloss measurement diameter changing mechanism and the like of the second embodiment.

The gloss measurement diameter changing mechanism 2000 includes, as illustrated, in FIGS. 12 to 14, an aperture plate 2010, a movement mechanism 2011, and the like. The aperture plate 2010 limits the light beam flux of the illumination light 1040. The movement mechanism 2011 moves the aperture plate 2010.

An area 2020 of the aperture plate 2010 is provided with an opening 2030. An area 2021 of the aperture plate 2010 is provided with an opening 2031. The diameter of the opening 2030 is smaller than that of the opening 2031. A light beam flux limiting mechanism in which the aperture plate 2010 is not easily called a plate may be used. The aperture plate 2010 is perpendicular to the optical axis 1110.

The aperture plate 2010 is moved by the movement mechanism 2011 to be located at a position in which the area 2020 indicated by the solid line of FIG. 12 and illustrated in FIG. 13 is located at the outside of the optical path of the illumination light 1040 and the area 2021 is located on the optical path of the illumination light 1040 or a position in which the area 2020 indicated by the one-dotted dash line illustrated in FIG. 12 and illustrated in FIG. 14 is located on the optical path of the illumination light 1040 and the area 2021 is located at the outside of the optical path of the illumination light 1040. The movement mechanism 2011 generates a force of moving the aperture plate 2010 and transmits the force of moving the aperture plate 2010 to the aperture plate 2010. The force of moving the aperture plate 2010 is generated by an electromagnetic motor, an electromagnetic actuator, a piezoelectric actuator, or the like.

When the area 2020 is located at the outside of the optical path of the illumination light 1040 and the area 2021 is located on the optical path of the illumination light 1040, the area 2021 overlaps the lens 1074 when viewed from the extension direction of the optical axis 1110 and the illumination light 1040 passing through the gloss measurement diameter changing mechanism 2000 passes through the opening 2031. In this case, the opening 2031 forms an opening through which the illumination light 1040 passes and the diameter of the opening through which the illumination light 1040 passes is determined by the diameter of the opening 2031.

When the area 2020 is located on the optical path of the illumination light 1040 and the area 2021 is located at the outside of the optical path of the illumination light 1040, the area 2020 overlaps the lens 1074 when viewed from the extension direction of the optical axis 1110 and the illumination light 1040 passing through the gloss measurement diameter changing mechanism 2000 passes through the opening 2030. In this case, the opening 2030 forms an opening through which the illumination light 1040 passes and the diameter of the opening through which the illumination light 1040 passes is determined by the diameter of the opening 2030.

The gloss measurement diameter changing mechanism 2000 changes the diameter of the opening through which the illumination light 1040 passes in two levels by changing an area on the optical path.

When the diameter of the opening through which the illumination light 1040 passes is changed, the diameter of the gloss measurement illumination target area is changed. When the diameter of the gloss measurement illumination target area is changed, the gloss measurement diameter is changed. When the diameter of the opening through which the illumination light 1040 passes is determined by the diameter of the opening 2031, the diameter of the gloss measurement illumination target area becomes the standard diameter and the gloss measurement diameter becomes the standard diameter. When the diameter of the opening through which the illumination light 1040 passes is determined by the diameter of the opening 2030, the diameter of the gloss measurement illumination target area becomes the small diameter and the gloss measurement diameter becomes the small diameter.

3 Third Embodiment

A third embodiment relates to a gloss measurement diameter changing mechanism to be used instead of the gloss measurement diameter changing mechanism of the first embodiment. A technology used in the other embodiment may be used in the third embodiment.

Figure 15:
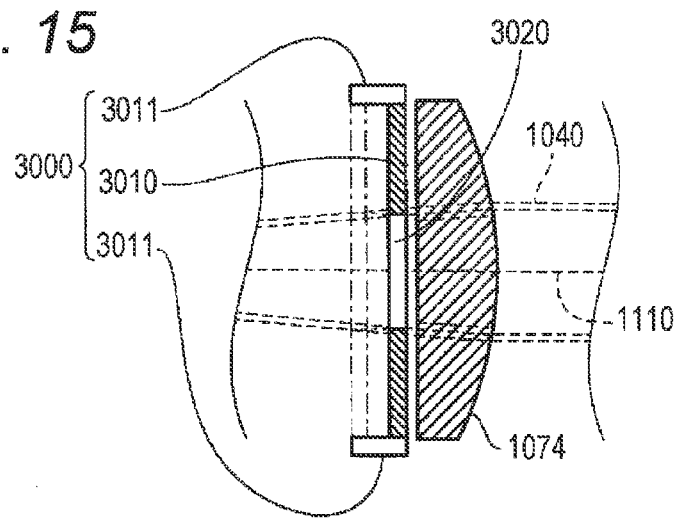
FIG. 15 is a cross-sectional view illustrating a gloss measurement diameter changing mechanism and the like of a third embodiment.

A schematic diagram of FIG. 15 is a cross-sectional view illustrating the gloss measurement diameter changing mechanism and the like.

The gloss measurement diameter changing mechanism 3000 includes, as illustrated in FIG. 15, an aperture plate 3010, a movement mechanism 3011, and the like. The aperture plate 3010 limits the light beam flux of the illumination light 1040. The movement mechanism 3011 moves the aperture plate 3010.

The aperture plate 3010 is provided with an opening 3020. The aperture plate 3010 is perpendicular to the optical axis 1110. A light beam flux limiting mechanism in which the aperture plate 3010 is not easily called a plate may be used.

The aperture plate 3010 is on the optical path of the illumination light 1040 and is moved by the movement mechanism 3011 to be located near the halogen lamp 1070 or the illumination target face 1050. The movement mechanism 3011 generates a force of moving the aperture plate 3010 and transmits the force of moving the aperture plate 3010 to the aperture plate 3010. The force of moving the aperture plate 3010 is generated by an electromagnetic motor, an electromagnetic actuator, a piezoelectric actuator, or the like.

The aperture plate 3010 overlaps the lens 1074 when viewed from the extension direction of the optical axis 1110. The illumination light 1040 which passes through the gloss measurement diameter changing mechanism 3000 passes through the opening 3020. The opening 3020 forms an opening through which the illumination light 1040 passes.

When the movement mechanism 3011 moves the aperture plate 3010 along the optical axis 1110 in parallel, the position of the opening 3020 is changed in two levels. The movement mechanism 3011 may change the position of the opening 3020 in three or more levels. The movement mechanism 3011 may continuously change the position of the opening 3020.

When the opening 3020 is moved along the optical axis 1110 in parallel, the opening angle of the light beam flux of the illumination light 1040 having passed through the opening 3020 is changed and the diameter of the gloss measurement illumination target area is changed. When the diameter of the gloss measurement illumination target area is changed, the gloss measurement diameter is changed. When the aperture plate 3010 is near the halogen lamp 1070, the opening angle of the light beam flux of the illumination light 1040 having passed through the opening 3020 relatively increases so that the diameter of the gloss measurement illumination target area becomes the standard diameter and the gloss measurement diameter becomes the standard diameter. When the aperture plate 3010 is near the illumination target face 1050, the opening angle of the light beam flux of the illumination light 1040 having passed through the opening 3020 relatively decreases so that the diameter of the gloss measurement illumination target area becomes the small diameter and the gloss measurement diameter becomes the small diameter.

4 Fourth Embodiment

4.1 Difference Between First Embodiment and Fourth Embodiment

A fourth embodiment relates to an interlocking mechanism to be used instead of the interlocking mechanism of the first embodiment. According to the interlocking mechanism of the first embodiment, the color measurement diameter is manually changed between the standard diameter and the small diameter and the gloss measurement diameter is automatically changed between the standard diameter and the small diameter in synchronization with a change in color measurement diameter. On the contrary, according to the interlocking mechanism of the fourth embodiment, the gloss measurement diameter is manually changed between the standard diameter and the small diameter and the color measurement diameter is automatically changed between the standard diameter and the small diameter in synchronization with a change in gloss measurement diameter. Hereinafter, only the different configuration will be described. A technology used in the other embodiment may be used in the fourth embodiment.

4.2 Gloss Measurement Diameter Changing Mechanism

Figure 16:
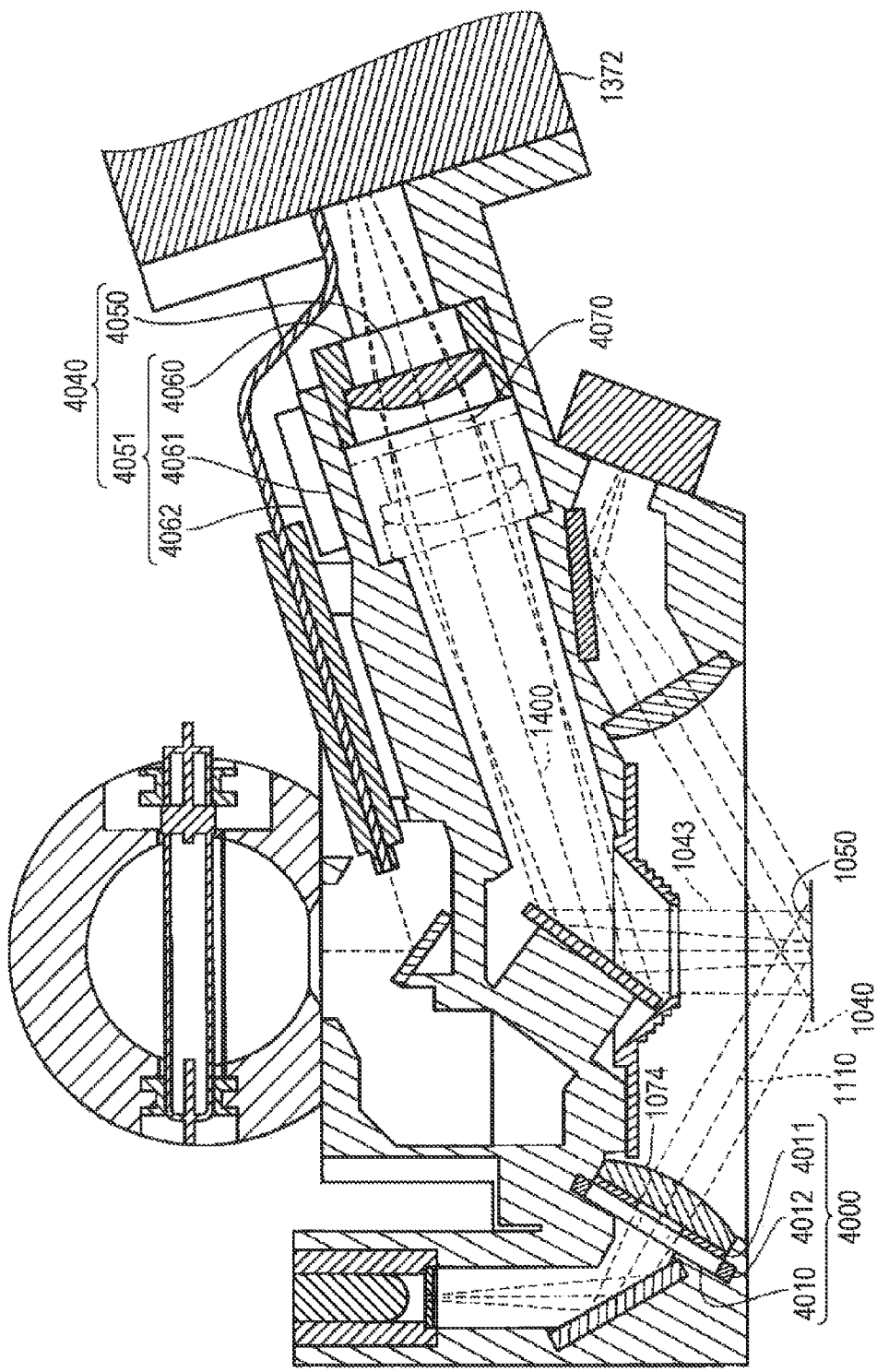
FIG. 16 is a cross-sectional view illustrating a measurement instrument of a fourth embodiment.

A schematic diagram of FIG. 16 is a cross-sectional view illustrating the measurement instrument equipped with the interlocking mechanism of the fourth embodiment. A schematic diagram of FIG. 17 is a front view illustrating the gloss measurement diameter changing mechanism and the like.

Figure 17:
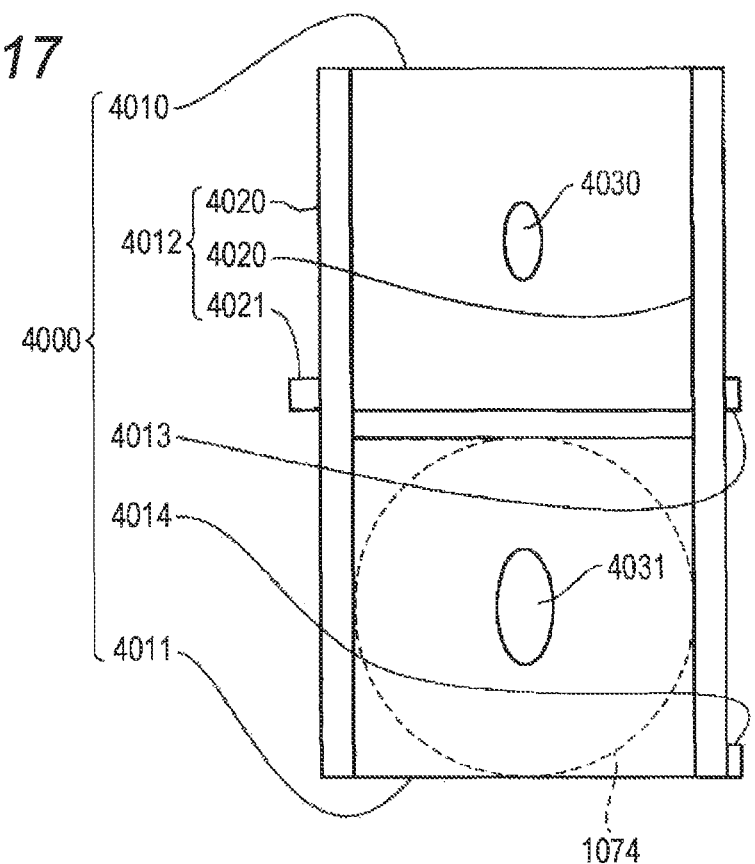
FIG. 17 is a cross-sectional view illustrating a gloss measurement diameter changing mechanism and the like of the fourth embodiment.

The gloss measurement diameter changing mechanism 4000 includes, as illustrated in FIGS. 16 and 17, an aperture plate 4010, an aperture plate 4011, a movement mechanism 4012, a limit switch 4013, a limit switch 4014, and the like. The aperture plate 4010 and the aperture plate 4011 are respectively the same as the aperture plate 1150 and the aperture plate 1151 of the first embodiment and limit the light beam flux of the illumination light 1040. The movement mechanism 4012 moves the aperture plate 4010. The limit switch 4013 and the limit switch 4014 detect the position of the aperture plate 4010.

The movement mechanism 4012 includes, a guide rail 4020, a knob 4021, and the like. The guide rail 4020 guides the aperture plate 4010. The knob 4021 transmits an applied force to the aperture plate 4010.

The aperture plate 4010 is provided with an opening 4030. The aperture plate 4011 is provided with an opening 4031. The diameter of the opening 4030 is smaller than that of the opening 4031.

The aperture plate 4010 is moved by the movement mechanism 4012 to be located at the outside of the optical path of the illumination light 1040 or to be located onto the optical path of the illumination light 1040. The aperture plate 4011 is fixed onto the optical path of the illumination light 1040.

The aperture plate 4010 is coupled to the guide rail 4020 and is slidable in the extension direction of the guide rail 4020. Accordingly, the extension direction of the aperture plate 4010 is regulated in the extension direction of the guide rail 4020 and the aperture plate 4010 is guided in the extension direction of the guide rail 4020. When a force is applied to the knob 4021, the applied force is transmitted to the aperture plate 4010 and the aperture plate 4010 moves in the extension direction of the guide rail 4020.

When the aperture plate 4010 is located at the outside of the optical path of the illumination light 1040, the opening 4031 forms an opening through which the illumination light 1040 passes and the diameter of the opening through which the illumination light 1040 passes is determined by the diameter of the opening 4031.

When the aperture plate 4010 is located on the optical path of the illumination light 1040, the opening 4030 and the opening 4031 form an opening through which the illumination light 1040 passes and the diameter of the opening through which the illumination light 1040 passes is determined by the diameter of the relatively small opening 4030.

The gloss measurement diameter changing mechanism 4000 changes the diameter of the opening through which the illumination light 1040 passes in two levels by inserting the aperture plate 4010 into the optical path of the illumination light 1040 or extracting the aperture plate from the optical path of the illumination light 1040.

When the diameter of the opening through which the illumination light 1040 passes is changed, the diameter of the gloss measurement illumination target area is changed. When the diameter of the gloss measurement illumination target area is changed, the gloss measurement diameter is changed. When the diameter of the opening through which the illumination light 1040 passes is determined by the size of the opening 4031, the diameter of the gloss measurement illumination target area becomes the standard diameter and the gloss measurement diameter becomes the standard diameter. When the diameter of the opening through which the illumination light 1040 passes is determined by the size of the opening 4030, the diameter of the gloss measurement illumination target area becomes the small diameter and the gloss measurement diameter becomes the small diameter.

The limit switch 4013 detects a state where the aperture plate 4010 is located at the outside of the optical path of the illumination light 1040. The limit switch 4014 detects a state where the aperture plate 4010 is located on the optical path of the illumination light 1040. When the aperture plate 4010 is located at the outside of the optical path of the illumination light 1040, the gloss measurement diameter becomes the standard diameter. Meanwhile, when the aperture plate 4010 is located on the optical path of the illumination light 1040, the gloss measurement diameter becomes the small diameter. For this reason, the gloss measurement diameter is determined by the position of the aperture plate 4010 and the limit switch 4013 and the limit switch 4014 output a detection result for the position of the aperture plate 4010 determining the gloss measurement diameter. A position of a constituent other than the aperture plate 4010 may be detected. For example, the position of the knob 4021 or the like may be detected. The position may be detected by a detection mechanism other than the limit switch 4013 and the limit switch 4014. For example, the position may be detected by a laser displacement gauge.

4.3 Color Measurement Diameter Changing Mechanism

The color measurement diameter changing mechanism 4040 includes as illustrated in FIG. 16, a lens 4050, a parallel movement mechanism 4051, and the like. The lens 4050 is the same as the lens 1390 of the first embodiment and converges the light beam flux of the reflected light 1043. The parallel movement mechanism 4051 moves the lens 4050 in parallel.

The parallel movement mechanism 4051 includes a lens holder 4060, a guide cylinder 4061, a driving mechanism 4062, and the like. The lens holder 4060 is the same as the lens holder 1420 of the first embodiment and holds the lens 4050. The guide cylinder 4061 is the same as the guide cylinder 1421 of the first embodiment and guides the lens holder 4060. The driving mechanism 4062 transmits a generated force to the lens holder 4060.

The lens holder 4060 is inserted into a guide hole 4070 formed in the guide cylinder 4061 and is slidable in the extension direction of the guide hole 4070. The extension direction of the guide hole 4070 matches the extension direction of the optical axis 1400. Accordingly, the movement direction of the lens 4050 is regulated in the extension direction of the optical axis 1400 and the lens 4050 is guided in the extension direction of the optical axis 1400. The driving mechanism 4062 generates a force of moving the lens holder 4060 and transmits the force of moving the lens holder 4060 to the lens holder 4060. The force of moving the lens holder 4060 is generated by an electromagnetic motor, an electromagnetic actuator, a piezoelectric actuator, or the like. When the driving mechanism 4062 transmits a force to the lens holder 4060, the lens 4050 and the lens holder 4060 move together along the optical axis 1400 in parallel.

The lens 4050 is moved in parallel by the parallel movement mechanism 4051 to be located near the spectral measurement instrument 1372 indicated by the solid line of FIG. 16 or the illumination target face 1050 indicated by the two-dotted dash line of FIG. 16.

When the parallel movement mechanism 4051 moves the lens 4050 along the optical axis 1400 in parallel, the position of the lens 4050 is changed in two levels.

When the lens 4050 is moved along the optical axis 1400 in parallel, the diameter of the light receiving target area of the color measurement is changed. When the diameter of the light receiving target area of the color measurement is changed, the color measurement diameter is changed.

When the lens 4050 is near the spectral measurement instrument 1372, the diameter of the light receiving target area of the color measurement becomes the standard diameter and the color measurement diameter becomes the standard diameter. When the lens 4050 is near the illumination target face 1050, the diameter of the light receiving target area of the color measurement becomes the small diameter and the color measurement diameter becomes the small diameter.

4.4 Interlocking Mechanism

Figure 18:
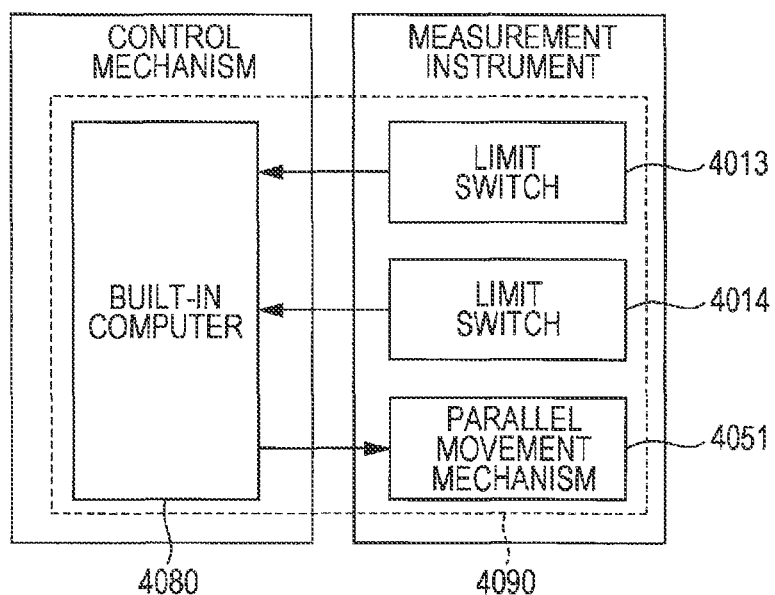
FIG. 18 is a block diagram illustrating an interlocking mechanism of the fourth embodiment.

A block diagram of FIG. 18 illustrates an interlocking mechanism.

A built-in computer 4080 acquires, as illustrated in FIG. 18, a detection result from the limit switch 4013 and the limit switch 4014. When the aperture plate 4010 is moved to the outside of the optical path of the illumination light 1040, the built-in computer 4080 moves the lens 4050 to a position near the spectral measurement instrument 1372 by the parallel movement mechanism 4051. When the aperture plate 4010 is moved onto the optical path of the illumination light 1040, the built-in computer 4080 moves the lens 4050 to a position near the illumination target face 1050 by the parallel movement mechanism 4051. Accordingly, an interlocking mechanism 4090 changing the color measurement diameter by the color measurement instrument 4074 in accordance with a detection result so that the color measurement diameter changes in synchronization with the gloss measurement diameter is formed. When the gloss measurement diameter is changed to the standard diameter, the color measurement diameter is changed to the standard diameter in synchronization with a change in gloss measurement diameter. When the gloss measurement diameter is changed to the small diameter, the color measurement diameter is changed to the small diameter in synchronization with a change in gloss measurement diameter. The color measurement diameter matches the gloss measurement diameter in synchronization with the gloss measurement diameter.

5 Fifth Embodiment

5.1 Difference Between First Embodiment and Fifth Embodiment

A fifth embodiment relates to an interlocking mechanism to be used instead of the gloss measurement interlocking mechanism of the first embodiment. According to the interlocking mechanism of the first embodiment, the color measurement diameter is manually changed between the standard diameter and the small diameter and the gloss measurement diameter is automatically changed between the standard diameter and the small diameter in synchronization with a change in color measurement diameter. On the contrary, according to the interlocking mechanism of the fifth embodiment, the gloss measurement diameter and the color measurement diameter are changed between the standard diameter and the small diameter in response to an operation of changing the measurement diameter. Hereinafter, only the different configuration will be described. A technology used in the other embodiment may be used in the fifth embodiment.

Figure 19:
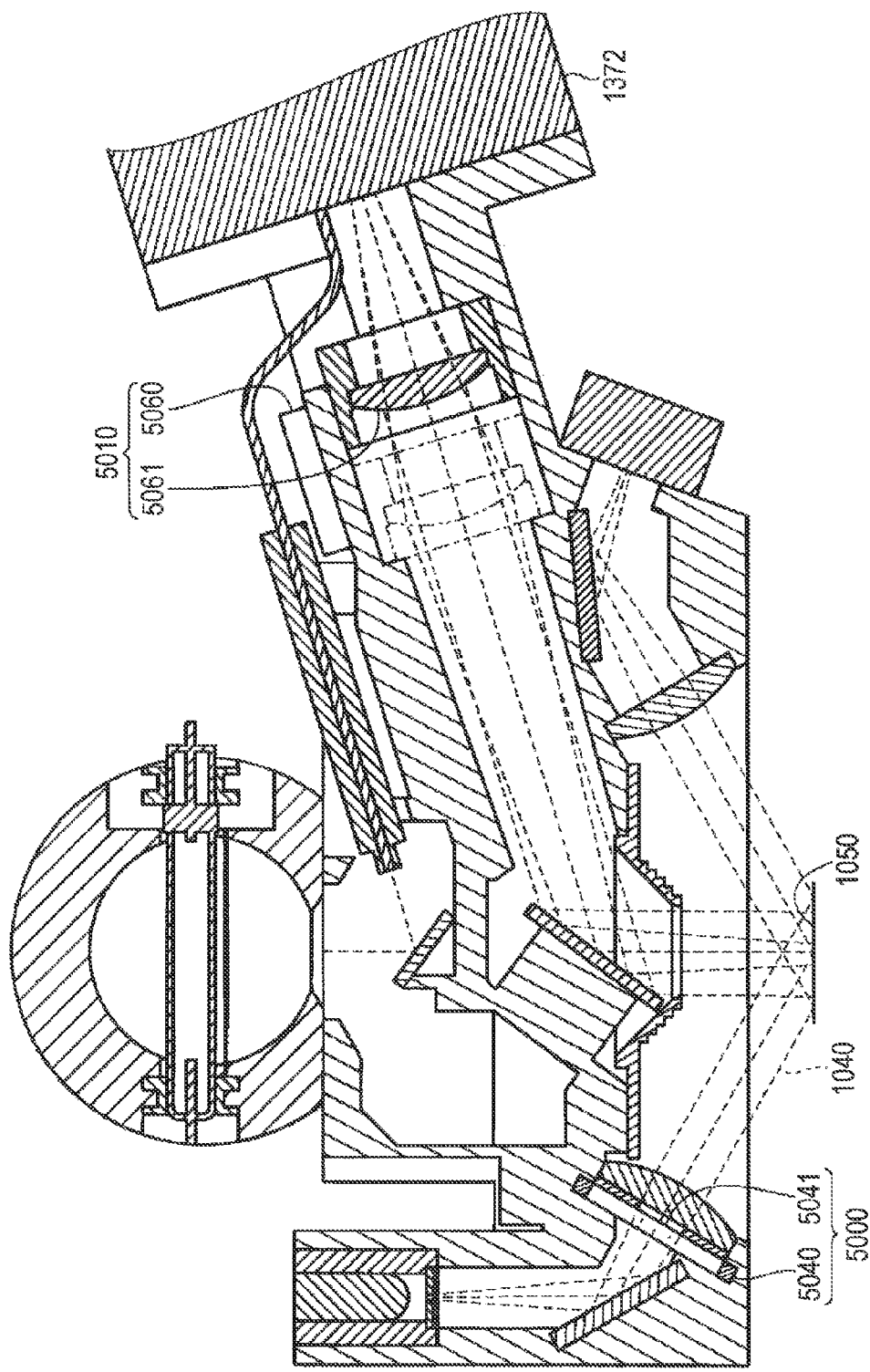
FIG. 19 is a cross-sectional view illustrating a measurement instrument of a fifth embodiment.

A schematic diagram of FIG. 19 is a cross-sectional view illustrating the measurement instrument equipped with the interlocking mechanism of the fifth embodiment. A block diagram of FIG. 20 illustrates an interlocking mechanism.

A gloss measurement diameter changing mechanism 5000 illustrated in FIG. 19 is the same as the gloss measurement diameter changing mechanism 1073 of the first embodiment. A color measurement diameter changing mechanism 5010 illustrated in FIG. 19 is the same as the color measurement diameter changing mechanism 4040 of the fourth embodiment.

Figure 20:
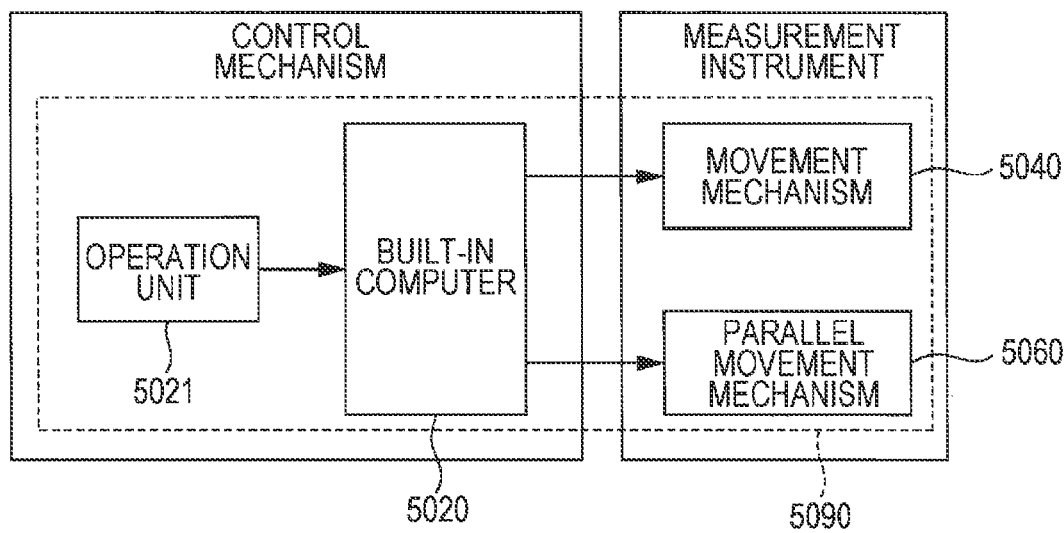
FIG. 20 is a block diagram illustrating an interlocking mechanism of the fifth embodiment.

A built-in computer 5020 acquires, as illustrated in FIG. 20, a detection result for an operation performed by a operation unit 5021. When the operation unit 5021 detects an operation of changing the measurement diameter to the standard diameter, the built-in computer 5020 moves the aperture plate 5041 to the outside of the optical path of the illumination light 1040 by a movement mechanism 5040 constituting the gloss measurement diameter changing mechanism 5000 and moves a lens 5061 to a positron near the spectral measurement instrument 1372 by a parallel movement mechanism 5060 constituting the color measurement diameter changing mechanism 5010. When the operation unit 5021 detects an operation of changing the measurement diameter to the small diameter, the built-in computer 5020 moves the aperture plate 5041 onto the optical path of the illumination light 1040 by the movement mechanism 5040 and moves the lens 5061 to a position near the illumination target face 1050 by the parallel movement mechanism 5060. Accordingly, an interlocking mechanism 5090 which changes the gloss measurement diameter by the gloss measurement instrument 5080 and changes the color measurement diameter by the color measurement instrument 5081 in accordance with a detection result for an operation of changing the measurement diameter is formed.

The operation unit 5021 is a switch, a touch panel, or the like and outputs a detection result for an operation of the gloss colorimeter. The operation unit may be replaced by a different detection mechanism. For example, the operation unit may be replaced by a communication unit which communicates with a device other than the gloss colorimeter and detects a detection result for an operation of the device. The device is, for example, a remote controller, a mobile communication terminal, a personal computer, or the like.

6 Sixth Embodiment

6.1 Difference Between Fifth Embodiment and Sixth Embodiment

A sixth embodiment relates to an independent changing mechanism to be used instead of the interlocking mechanism of the fifth embodiment. According to the interlocking mechanism of the fifth embodiment, the gloss measurement diameter and the color measurement diameter are changed between the standard diameter and the small diameter in response to an operation of changing the measurement diameter. On the contrary, according to the independent changing mechanism of the sixth embodiment, the gloss measurement diameter is changed between the standard diameter and the small diameter and the color measurement diameter is changed between the standard diameter and the small diameter independently from the gloss measurement diameter. Hereinafter, only the different configuration will be described. A technology used in the other embodiment may be used in the sixth embodiment.

Figure 21:
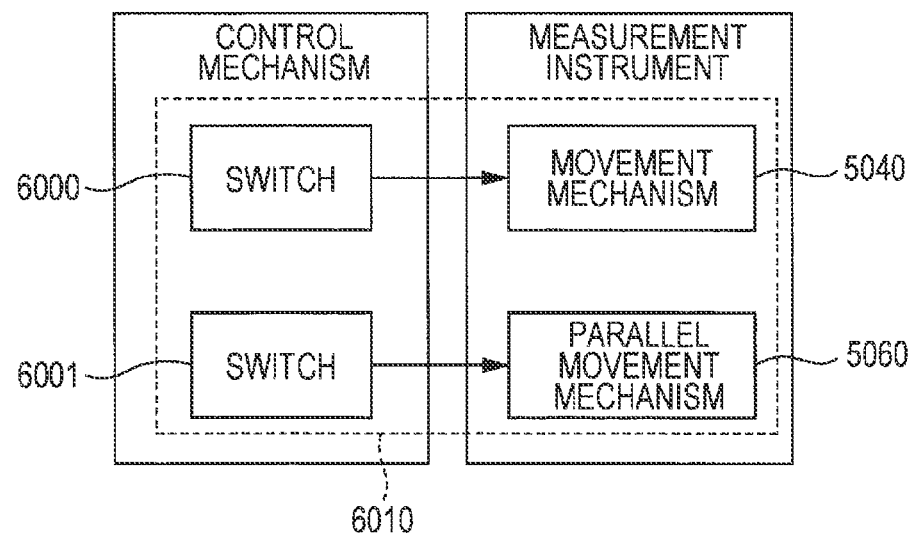
FIG. 21 is a block diagram illustrating an independent changing mechanism of a sixth embodiment.

A block diagram of FIG. 21 illustrates an independent changing mechanism.

When a switch 6000 is operated to change the gloss measurement diameter to the standard diameter, the movement mechanism 5040 moves the aperture plate 5041 to the outside of the optical path of the illumination light 1040. When the switch 6000 is operated to change the gloss measurement diameter to the small diameter, the movement mechanism 5040 moves the aperture plate 5041 onto the optical path of the illumination light 1040. When the switch 6001 is operated to change the color measurement diameter to the standard diameter, the parallel movement mechanism 5060 moves the lens 5061 to a position near the spectral measurement instrument 1372. When the switch 6001 is operated to change the color measurement diameter to the small diameter, the parallel movement mechanism 5060 moves the lens 5061 to a position near the illumination target face 1050. Accordingly, an independent changing mechanism 6010 is formed.

The present invention has been described in detail, but the above-described technology is merely an example. Thus, it should be understood that various corrections and modifications can be made without departing from the scope of the present invention.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

REFERENCE SIGNS LIST

1000: gloss colorimeter
1020: gloss measurement instrument
1021: color measurement instrument
1030: gloss measurement illumination mechanism
1031: gloss measurement light receiving mechanism
1032: color measurement illumination mechanism
1033: color measurement light receiving mechanism
1073, 2000, 3000, 4000, 5000: gloss measurement diameter changing mechanism
1371, 4040, 5010: color measurement diameter changing mechanism

The invention claimed is:

1. A surface characteristic measurement device comprising:
   a gloss measurement instrument that comprises a first light source and a first mirror and that:
      illuminates an illumination target face by first illumination light,
      receives first reflected light generated by a regular reflection of the first illumination light on the illumination target face, and
      outputs a measurement result for the first reflected light;
   a color measurement instrument that comprises a second light source and a second mirror and that:
      illuminates the illumination target face by second illumination light,
      receives second reflected light generated by a reflection of the second illumination light on the illumination target face,
      outputs a measurement result for the second reflected light, and outputs a detection result related to a size of a measurement target area including a reflection characteristic measurement target area and a gloss measurement target area; and
a controller,
wherein
a size of the reflection characteristic measurement target area is adjustable by the color measurement instrument,
a size of the gloss measurement target area is adjustable by the gloss measurement instrument,
the controller changes the size of the gloss measurement target area by the gloss measurement instrument or changes the size of the reflection characteristic measurement target area by the color measurement instrument in accordance with the detection result, and
the color measurement instrument is integrated with the gloss measurement instrument.

2. The surface characteristic measurement device according to claim 1, wherein
the gloss measurement instrument:
illuminates an illumination target area of the illumination target face by the first illumination light and changes a size of the illumination target area to change the size of the gloss measurement target area, and
receives the first reflected light and outputs a measurement result for the first reflected light.

3. The surface characteristic measurement device according to claim 2, wherein
the first light source emits the first illumination light, and
the gloss measurement instrument further comprises an opening through which the first illumination light passes and changes a size of the opening to change a size of the illumination target area.

4. The surface characteristic measurement device according to claim 2, wherein
the first light source emits the first illumination light, and
the gloss measurement instrument further comprises an opening through which the first illumination light passes and moves the opening along an optical axis of the first light source in parallel to change the size of the illumination target area.

5. The surface characteristic measurement device according to claim 1, wherein
the color measurement instrument:
illuminates the illumination target face by the second illumination light,
receives the second reflected light generated by a reflection of the second illumination light on a light receiving target area of the illumination target face,
outputs a measurement result for the second reflected light, and
changes a size of the light receiving target area to change the size of the reflection characteristic measurement target area.

6. A surface characteristic measurement device comprising:
a gloss measurement instrument that comprises a first light source and a first mirror and that:
illuminates an illumination target face by first illumination light,
receives first reflected light generated by a regular reflection of the first illumination light on the illumination target face, and
outputs a measurement result for the first reflected light; and a color measurement instrument that comprises a second light source and a second mirror and that:
illuminates the illumination target face by second illumination light,
receives second reflected light generated by a reflection of the second illumination light on the illumination target face, and
outputs a measurement result for the second reflected light,
wherein
a size of a reflection characteristic measurement target area is adjustable by the color measurement instrument,
a size of a gloss measurement target area is adjustable by the gloss measurement instrument, and
the color measurement instrument is integrated with the gloss measurement instrument,
the color measurement instrument:
illuminates the illumination target face by the second illumination light,
receives the second reflected light generated by a reflection of the second illumination light on a light receiving target area of the illumination target face,
outputs a measurement result for the second reflected light, and
changes a size of the light receiving target area to change the size of the reflection characteristic measurement target area, and
the color measurement instrument:
further comprises a lens,
changes the size of the light receiving target area so that the second reflected light passes through the lens, the lens converges a light beam flux of the second reflected light, and the lens moves in parallel along an optical axis of the second light source, and
receives the second reflected light after the second reflected light passes through the lens.

7. The surface characteristic measurement device according to claim 1, wherein
the color measurement instrument outputs, as the detection result, a position of a constituent determining the size of the gloss measurement target area; and
the controller changes the size of the reflection characteristic measurement target area by the color measurement instrument in accordance with the detection result so that the size of the reflection characteristic measurement target area changes in synchronization with a change in the size of the gloss measurement target area.

8. The surface characteristic measurement device according to claim 1, wherein
the color measurement instrument outputs, as the detection result, a position of a constituent determining the size of the reflection characteristic measurement target area; and
the controller changes the size of the gloss measurement target area by the gloss measurement instrument in accordance with the detection result so that the size of the gloss measurement target area changes in synchronization with the size of the reflection characteristic measurement target area.

9. The surface characteristic measurement device according to claim 1, wherein
the color measurement instrument outputs, as the detection result, an operation of changing the size of the measurement target area; and
the controller changes the size of the gloss measurement target area by the gloss measurement instrument and changes the size of the reflection characteristic measurement target area by the color measurement instrument in accordance with the detection result.

10. The surface characteristic measurement device according to claim 1, wherein the reflection characteristic measurement is a color measurement.

11. The surface characteristic measurement device according to claim 1, wherein a reflection characteristic measurement illumination target area illuminated by the second illumination light overlaps a gloss measurement illumination target area illuminated by the first illumination light.

12. The surface characteristic measurement device according to claim 2, wherein
the color measurement instrument:
illuminates the illumination target face by the second illumination light,
receives the second reflected light generated by a reflection of the second illumination light on a light receiving target area of the illumination target face,
outputs a measurement result for the second reflected light, and
changes a size of the light receiving target area to change the size of the reflection characteristic measurement target area.

13. The surface characteristic measurement device according to claim 2, wherein
the color measurement instrument outputs, as the detection result, a position of a constituent determining the size of the gloss measurement target area; and
the controller changes the size of the reflection characteristic measurement target area by the color measurement instrument in accordance with the detection result so that the size of the reflection characteristic measurement target area changes in synchronization with a change in the size of the gloss measurement target area.

14. The surface characteristic measurement device according to claim 2, wherein
the color measurement instrument outputs, as the detection result, a position of a constituent determining the size of the reflection characteristic measurement target area; and
the controller changes the size of the gloss measurement target area by the gloss measurement instrument in accordance with the detection result so that the size of the gloss measurement target area changes in synchronization with the size of the reflection characteristic measurement target area.

15. The surface characteristic measurement device according to claim 2, wherein
the control measurement instrument outputs, as the detection result, an operation of changing the size of a measurement target area; and
the controller changes the size of the gloss measurement target area by the gloss measurement instrument and changes the size of the reflection characteristic measurement target area by the color measurement instrument in accordance with the detection result.

16. The surface characteristic measurement device according to claim 2, wherein the reflection characteristic measurement is a color measurement.

17. The surface characteristic measurement device according to claim 2, wherein a reflection characteristic measurement illumination target area illuminated by the second illumination light overlaps a gloss measurement illumination target area illuminated by the first illumination light.

18. The surface characteristic measurement device according to claim 3, wherein
the color measurement instrument:
illuminates the illumination target face by the second illumination light,
receives the second reflected light generated by a reflection of the second illumination light on a light receiving target area of the illumination target face,
outputs a measurement result for the second reflected light, and
changes a size of the light receiving target area to change the size of the reflection characteristic measurement target area.

19. The surface characteristic measurement device according to claim 3, wherein
the color measurement instrument outputs, as the detection result, a position of a constituent determining the size of the gloss measurement target area; and
the controller changes the size of the reflection characteristic measurement target area by the color measurement instrument in accordance with the detection result so that the size of the reflection characteristic measurement target area changes in synchronization with a change in the size of the gloss measurement target area.

20. The surface characteristic measurement device according to claim 3, wherein
the color measurement instrument outputs, as the detection result, a position of a constituent determining the size of the reflection characteristic measurement target area; and
the controller changes the size of the gloss measurement target area by the gloss measurement instrument in accordance with the detection result so that the size of the gloss measurement target area changes in synchronization with the size of the reflection characteristic measurement target area.

* * * * *